(12) United States Patent
MacDonald et al.

(10) Patent No.: US 11,345,935 B2
(45) Date of Patent: *May 31, 2022

(54) LOW TEMPERATURE PRETREATMENT WITH SULFUR DIOXIDE

(71) Applicant: Iogen Corporation, Ottawa (CA)

(72) Inventors: Daniel G. MacDonald, Orleans (CA); Jeffrey S. Tolan, Ottawa (CA); Brian Foody, Ottawa (CA)

(73) Assignee: Iogen Corporation, Ontario (CA)

( * ) Notice: Subject to any disclaimer, the term of this patent is extended or adjusted under 35 U.S.C. 154(b) by 21 days.

This patent is subject to a terminal disclaimer.

(21) Appl. No.: 16/761,192

(22) PCT Filed: Nov. 9, 2018

(86) PCT No.: PCT/CA2018/000217
§ 371 (c)(1),
(2) Date: May 1, 2020

(87) PCT Pub. No.: WO2019/090414
PCT Pub. Date: May 16, 2019

(65) Prior Publication Data
US 2020/0263209 A1    Aug. 20, 2020

Related U.S. Application Data

(60) Provisional application No. 62/725,583, filed on Aug. 31, 2018, provisional application No. 62/583,705, filed on Nov. 9, 2017.

(51) Int. Cl.
*C12P 7/10* (2006.01)
*C12P 19/02* (2006.01)
*C12P 19/14* (2006.01)

(52) U.S. Cl.
CPC ............... *C12P 7/10* (2013.01); *C12P 19/02* (2013.01); *C12P 19/14* (2013.01); *C12P 2201/00* (2013.01)

(58) Field of Classification Search
CPC .... C12P 7/10; C12P 7/06; C12P 19/02; C12P 19/14; C12P 2201/00
See application file for complete search history.

(56) References Cited

U.S. PATENT DOCUMENTS

| | | |
|---|---|---|
| 2,060,068 A | 11/1936 | Groombridge et al. |
| 2,418,167 A | 4/1947 | Bois |
| 2,710,254 A | 6/1955 | Van Blaricom et al. |
| 2,710,255 A | 6/1955 | Van Blaricom et al. |
| 3,046,182 A | 11/1956 | Tomlinson et al. |
| 3,148,177 A | 9/1964 | Wiley et al. |
| 3,251,820 A | 5/1966 | Grangaard |
| 3,297,676 A | 1/1967 | Brauns |
| 4,295,929 A | 10/1981 | Leithem |
| 4,336,189 A | 6/1982 | Hamala et al. |
| 4,461,648 A | 7/1984 | Foody |
| 4,631,129 A | 12/1986 | Heikkila |
| 4,988,799 A | 1/1991 | Samson et al. |
| 5,096,540 A | 3/1992 | Sell et al. |
| 5,424,417 A | 6/1995 | Torget et al. |
| 5,637,225 A | 6/1997 | Heikkila et al. |
| 5,777,086 A | 7/1998 | Klyosov et al. |
| 5,789,210 A | 8/1998 | Ho et al. |
| 5,866,382 A | 2/1999 | Hallborn et al. |
| 6,475,768 B1 | 11/2002 | Otero et al. |
| 6,582,944 B1 | 6/2003 | Hallborn et al. |
| 7,198,925 B2 | 4/2007 | Foody |
| 7,527,927 B1 | 5/2009 | Ho et al. |
| 7,527,951 B2 | 5/2009 | Londesborough et al. |
| 7,585,652 B2 | 9/2009 | Foody et al. |
| 7,622,284 B2 | 11/2009 | Op Den Camp et al. |
| 7,709,042 B2 | 5/2010 | Foody et al. |
| 7,754,456 B2 | 7/2010 | Penttila et al. |
| 7,754,457 B2 | 7/2010 | Foody et al. |
| 7,901,511 B2 | 3/2011 | Griffin et al. |
| 7,993,463 B2 | 8/2011 | Griffin et al. |
| 8,017,361 B2 | 9/2011 | Scott et al. |
| 8,017,820 B2 | 9/2011 | Foody et al. |
| 8,038,842 B2 | 10/2011 | Retsina et al. |
| 8,252,568 B2 | 8/2012 | Foody et al. |
| 8,268,125 B2 | 9/2012 | Retsina et al. |
| 8,328,947 B2 | 12/2012 | Anand et al. |

(Continued)

FOREIGN PATENT DOCUMENTS

| | | |
|---|---|---|
| EP | 0450430 B1 | 10/1991 |
| EP | 0715657 B1 | 6/1996 |

(Continued)

OTHER PUBLICATIONS

U.S. Appl. No. 16/761 180 (Year: 2020).*
U.S. Appl. No. 17/040 738 (Year: 2020).*
U.S. Appl. No. 17/271 392 (Year: 2021).*
Auxenfans et al., "Understanding the structural and chemical changes of plant biomass following steam explosion pretreatment," Biotechnol. Biofuels, 2017, vol. 10, No. 36.
Balan, V., "Current Challenges in Commercially Producing Biofuels from Lignocellulosic Biomass" ISRN Biotechnology, 2014, Article No. 463074.
Behera et al., "Importance of chemical pretreatment for bioconversion of lignocellulosic biomass" 2014, Renewable and Sustainable Energy Reviews, pp. 91-106, vol. 36.
Benjamin et al., "A General Description of Commercial Wood Pulping and Bleaching Processes", Journal of the Air Pollution Control Association, 1969, pp. 155-161vol. 19, No. 3.

(Continued)

*Primary Examiner* — Ruth A Davis
(74) *Attorney, Agent, or Firm* — Knobbe, Martens, Olson & Bear, LLP

(57) ABSTRACT

A process for producing a fuel from lignocellulosic biomass is disclosed. The process includes obtaining a feedstock comprising lignocellulosic biomass, feeding the feedstock and sulfur dioxide into a pretreatment reactor, wherein a total amount of sulfur dioxide in the pretreatment reactor is greater than 70 wt % based on dry weight lignocellulosic biomass, and heating the feedstock and sulfur dioxide in the pretreatment reactor at one or more temperatures between 110° C. and 150° C. for more than 60 minutes.

25 Claims, 9 Drawing Sheets

(56) References Cited

U.S. PATENT DOCUMENTS

| | | |
|---|---|---|
| 8,409,836 B2 | 4/2013 | Vehmaanpera et al. |
| 8,603,789 B2 | 12/2013 | Harlick |
| 8,709,770 B2 | 4/2014 | Harlick et al. |
| 8,728,243 B2 | 5/2014 | Van Der Meulen et al. |
| 8,815,499 B2 | 8/2014 | Alriksson et al. |
| 8,815,561 B2 | 8/2014 | Liu et al. |
| 8,834,633 B2 | 9/2014 | Van Der Meulen et al. |
| 8,835,156 B2 | 9/2014 | Bjornsson et al. |
| 8,853,478 B2 | 10/2014 | Machhammer et al. |
| 8,871,475 B2 | 10/2014 | Alriksson et al. |
| 8,993,274 B2 | 3/2015 | Romero |
| 9,012,188 B2 | 4/2015 | Van Heiningen et al. |
| 9,068,236 B2 | 6/2015 | Heikkila et al. |
| 9,074,231 B2 | 7/2015 | Zhu |
| 9,090,915 B2 | 7/2015 | Wang et al. |
| 9,102,951 B2 | 8/2015 | Griffin et al. |
| 9,212,401 B2 | 12/2015 | Weider et al. |
| 9,243,364 B2 | 1/2016 | Zhu et al. |
| 9,284,382 B2 | 3/2016 | Chen et al. |
| 9,290,821 B2 | 3/2016 | Blackbourn et al. |
| 9,303,253 B2 | 4/2016 | Van Maris et al. |
| 9,399,840 B2 | 7/2016 | Nelson et al. |
| 9,434,961 B2 | 9/2016 | Dottori et al. |
| 9,624,436 B2 | 1/2017 | Hamilton et al. |
| 9,574,212 B2 | 2/2017 | Foody et al. |
| 9,631,316 B2 | 4/2017 | Retsina et al. |
| 9,738,729 B2 | 8/2017 | Retsina et al. |
| 9,783,565 B2 | 10/2017 | Carlius et al. |
| 9,856,605 B2 | 1/2018 | Retsina |
| 9,873,665 B2 | 1/2018 | Blackbourn et al. |
| 10,144,939 B2 | 12/2018 | Noodam et al. |
| 10,316,336 B2 | 6/2019 | Survase et al. |
| 10,421,667 B2 | 9/2019 | Foody et al. |
| 10,513,714 B2 | 12/2019 | Foody et al. |
| 10,513,715 B2 | 12/2019 | Foody et al. |
| 10,655,149 B2 | 5/2020 | Dechman et al. |
| 10,662,455 B2 | 5/2020 | Tolan et al. |
| 10,995,314 B2 | 5/2021 | Foody et al. |
| 11,008,598 B2 | 5/2021 | Foody et al. |
| 2007/0254348 A1 | 9/2007 | Retsina et al. |
| 2009/0118477 A1 | 5/2009 | Hallberg et al. |
| 2010/0056774 A1 | 3/2010 | Anand et al. |
| 2010/0279361 A1 | 11/2010 | South et al. |
| 2011/0165643 A1 | 7/2011 | Retsina et al. |
| 2011/0207922 A1 | 8/2011 | Kubo et al. |
| 2011/0250638 A1 | 10/2011 | Sjoede et al. |
| 2011/0300586 A1 | 12/2011 | Liu et al. |
| 2012/0041186 A1 | 2/2012 | Pschorn et al. |
| 2012/0073199 A1 | 3/2012 | Lewis |
| 2012/0315674 A1 | 12/2012 | Realff et al. |
| 2013/0071903 A1 | 3/2013 | Rowland et al. |
| 2013/0118483 A1 | 5/2013 | Gao et al. |
| 2014/0024093 A1 | 1/2014 | Blackbourn et al. |
| 2014/0034047 A1 | 2/2014 | Retsina et al. |
| 2014/0053827 A1 | 2/2014 | Macedo Baudel et al. |
| 2014/0142351 A1 | 5/2014 | Johnston et al. |
| 2014/0154746 A1 | 6/2014 | Jonsson et al. |
| 2014/0163210 A1 | 6/2014 | Retsina et al. |
| 2014/0178944 A1 | 6/2014 | Parekh et al. |
| 2014/0182582 A1 | 7/2014 | Retsina et al. |
| 2014/0186899 A1 | 7/2014 | Retsina et al. |
| 2014/0186901 A1 | 7/2014 | Retsina et al. |
| 2014/0186903 A1 | 7/2014 | Retsina et al. |
| 2015/0047629 A1 | 2/2015 | Borden et al. |
| 2015/0225756 A1 | 8/2015 | Retsina et al. |
| 2015/0259709 A1 | 9/2015 | Retsina et al. |
| 2015/0299738 A1 | 10/2015 | Wang et al. |
| 2015/0299739 A1 | 10/2015 | Harlick et al. |
| 2016/0152779 A1 | 6/2016 | Pylkkanen et al. |
| 2016/0237102 A1 | 8/2016 | Retsina et al. |
| 2016/0237173 A1 | 8/2016 | Nelson et al. |
| 2016/0257979 A1 | 9/2016 | Retsina et al. |
| 2016/0281298 A1 | 9/2016 | Nelson et al. |
| 2017/0002387 A1 | 1/2017 | Retsina et al. |
| 2017/0211231 A1 | 7/2017 | Baker et al. |
| 2018/0016607 A1 | 1/2018 | Hagglund |
| 2018/0037862 A1 | 2/2018 | Foody et al. |
| 2018/0037863 A1 | 2/2018 | Foody et al. |
| 2018/0037915 A1 | 2/2018 | Foody et al. |
| 2019/0127275 A1 | 5/2019 | Andresen et al. |
| 2019/0271114 A1 | 9/2019 | Nelson et al. |

FOREIGN PATENT DOCUMENTS

| | | |
|---|---|---|
| WO | WO 89/08165 | 9/1989 |
| WO | WO2010/078930 | 7/2010 |
| WO | WO 2013/113579 A1 | 8/2013 |
| WO | WO 2015/103197 | 7/2015 |
| WO | WO 2016/113221 | 7/2016 |
| WO | WO 2017/112471 A1 | 6/2017 |
| WO | WO 2020/093131 | 5/2020 |
| WO | WO 2020/223792 | 11/2020 |

OTHER PUBLICATIONS

Bensah, E. and Mensah, M., "Chemical Pretreatment Methods for the Production of Cellulosic Ethanol: Technologies and Innovations," International Journal of Chemical Engineering, 2013, pp. 1-21, vol. 2013.

Bhalla et al., "Improved lignocellulose conversion to biofuels with thermophilic bacteria and thermostable enzymes," Bioresource Technology, 2013, pp. 751-759, vol. 128.

Boussaid et al., "Fermentability of the Hemicellulose-Derived Sugars from Steam-Exploded Softwood (Douglas Fir)," Biotechnology and Bioengineering, 1999, pp. 284-289, vol. 64, No. 3.

Brownell, H. and Saddler, J., "Steam Pretreatment of Lignocellulosic Material for Enhanced Enzymatic Hydrolysis," Biotechnology and Bioengineering, 1987, pp. 228-235, vol. 29.

Bruijnincx et al., "Lignin Valorisation The Importance of a Full Value Chain Approach," APC, 2016.

Bu et al., "Comparative Study of Sulfite Pretreatments for Robust Enzymatic Saccharification of Corn Cob Residue," Biotechnology for Biofuels, 2012, vol. 5, No. 87.

Bura et al., "Influence of Xylan on the Enzymatic Hydrolysis of Steam-Pretreated Corn Stover and Hybrid Poplar," Biotechnol Prog, 2009, pp. 315-322, vol. 25, No. 2.

Bura et al., "Moving towards commercialization of lignocellulosic biomass to fuels to chemicals. How to deal with heterogeneous biomass?" University of Washington Biofuels and Bioproducts Laboratory, 2012.

Bura et al., "Optimization of SO2-Catalyzed Steam Pretreatment of Corn Fiber for Ethanol Production", Applied Biochemistry and Biotechnology, 2003, vol. 105-108, pp. 319-335.

Bura et al., "SO2-Catalyzed Steam Explosion of Corn Fiber for Ethanol Production," Applied Biochemistry and Biotechnology, 2002, pp. 59-72, vols. 98-100.

Carrasco et al., "SO2-catalysed steam pretreatment of quinoa stalks," J Chem Technol Biotechnol, 2015, pp. 64-71, vol. 90.

Carrasco et al., "SO2-catalyzed steam pretreatment and fermentation of enzymatically hydrolyzed sugarcane bagasse," Enzyme and Microbial Technology, 2010, pp. 64-73, vol. 46.

Carrasco, "Arabinosylated phenolics obtained from S02-steam-pretreated sugarcane bagasse," Journal of Chemical Technology and Biotechnology, 2012, pp. 1723-1726, vol. 87.

Chacha et al., "Steam Pretreatment of Pine (Pinus patula) Wood Residue for the Production of Reducing Sugars," Cellulose Chemistry and Technology, 2011, pp. 495-501, vol. 45 (7-8).

Chandra et al., "Enhancing Hemicellulose Recovery and the Enzymatic Hydrolysis of Cellulose by Adding Lignosulfonates during the Two-Stage Steam Pretreatment of Poplar," ACS Sustainable Chem Eng, 2015, pp. 986-991, vol. 3.

Cheng et al., "High titer and yield ethanol production from undetoxified whole slurry of Douglas-fir forest residue using pH profiling in SPORL," Biotechnology for Biofuels, 2015, pp. 1-10, vol. 8:22.

Chum et al., "Pretreatment—Catalyst Effects and the Combined Severity Parameter," Appl. Biochem. and Biotech., 1990, vol. 24/25.

(56) References Cited

OTHER PUBLICATIONS

Chylenski et al., "Enzymatic degradation of sulfite-pulped softwoods and the role of LPMOs," Biotechnol. Biofuels, 2017, 10/177.

Clark et al., "Steam Explosion of the Softwood Pinus Radiata with Sulphur Dioxide Addition. II. Process Characterisation," Journal of Wood Chemistry and Technology, 1989, pp. 135-166, vol. 9:2.

Clark et al., "Steam Explosion of the Softwood Pinus Radiata with Sulphur Dioxide Addition. I. Process Optimization," Journal of Wood Chemistry and Technology, 1987, pp. 373-403, vol. 7:3.

Corrales et al., "Structural evaluation of sugar cane bagasse steam pretreated in the presence of CO2 and SO2," Biotechnology for Biofuels, 2012, pp. 1-8, vol. 5:36.

De Bari et al., "SO2-Catalyzed Steam Fractionation of Aspen Chips for Bioethanol Production: Optimization of the Catalyst Impregnation," Ind. Eng. Chem. Res, 2007, pp. 7711-7720, vol. 46.

Dekker, R.F.H. et al., "Enzymic Saccharification of Sugarcane Bagasse Pretreated by Autohydrolysis-Steam Explosion," Biotechnology and Bioengineering, 1983, pp. 3027-3048, vol. XXV.

Dekker, Robert F. H., "The Utilization of Autohydrolysis-Exploded Hardwood (Eucalyptus Regnans) and Softwood (Pinus Radiata) Sawdust for the Production of Cellulolytic Enzymes and Fermentable Substrates," Biocatalysis, 1987, pp. 63-75, vol. 1.

Deshpande et al., "The reactivity of lignin carbohydrate complex (LCC) during manufacture of dissolving pulp from softwood," Industrial Crops & Products, 2018, pp. 315-322, vol. 115.

Deshpande et al., "The influence of Different Types of Bisulfite Cooking Liquors on Pine Wood Components," BioResources, 2016, pp. 5961-5973, vol. 11. No. 3.

Deshpande, R., "The initial phase of sodium sulfite pulping of softwood", Doctoral Thesis, Karlstad University Studies, 2016.

Ehsanipour, Mandana, "Bioconversion of lignocellulosic hydrolysate to acetic acid using Moorella thermoacetica," a thesis submitted in partial fulfillment of the requirements for the degree of Master of Science at University of Washington, 2015.

Eklund et al., "The Influence of SO2 and H2SO4 Impregnation of Willow Prior to Steam Pretreatment," 1995, Bioresource Engineering, pp. 225-229, vol. 52.

Elander et al., "Summary of findings from the Biomass Refining Consortium for Applied Fundamentals and Innovation (CAFI): corn stover pretreatment," 2009, Cellulose, pp. 649-659 vol. 16.

Ewanick et al., "The effect of biomass moisture content on bioethanol yields from steam pretreated switchgrass and sugarcane bagasse," 2011, Bioresource Technology, pp. 2651-2658, vol. 102.

Fan et al., "Optimization of SO2-catalyzed hydrolysis of corncob for xylose and xylitol production," 2014, J Chem Technol Biotechnol, pp. 1720-1726, vol. 89.

Fatehi et al., "Extraction of Technical Lignins from Pulping Spent Liquors, Challenges and Opportunities," Chapter 2 Production of Biofuels and Chemicals from Lignin, 2016, pp. 35-54.

Felby et al., "Ethanol from Wheat Straw Cellulose by Wet Oxidation Pretreatment and Simultaneous Saccharification and Fermentation", American Chemical Society, ACS Symposium Series, 2003, pp. 157-174.

Frolander, et al., "Conversion of cellulose, hemicellulose and lignin into platform molecules: biotechnological approach," Eurobioref. 2011.

Galbe et al., "A review of the production of ethanol from softwood," 2002, Appl Microbial Biotechnol, pp. 618-628, vol. 59.

Gao et al., "Lignin triggers irreversible cellulase loss during pretreated lignocellulosic biomass saccharification," Biotechnology for Biofuels, 2014, vol. 14, No. 175.

Gao et al., "Saccharification of recalcitrant biomass and integration options for lignocellulosic sugars from Catchlight Energy's sugar process (CLE Sugar)," Biotechnology for Biofuels, 2013, vol. 6, No. 10.

Garlock et al., "Comparative material balances around pretreatment technologies for the conversion of switchgrass to soluble sugars," 2011, Bioresource Technology, pp. 11063-11071, vol. 102.

Gelosia et al., "Fractionation of Lignocellulosic Residues Coupling Steam Explosion and Organosolv Treatments Using Green Solvent Valerolactone," Energies, 2017, vol. 10.

Gregg et al., "A Techno-Economic Assessment of the Pretreatment and Fractionism Steps of a Biomass-to-Ethanol Process," 1996, Applied Biochemistry and Biotechnology, pp. 711-727, vol. 57/58.

Gu et al., "Fermentative High-Titer Ethanol Production from Douglas-Fir Forest Residue Without Detoxification Using SPORL: High SO2 Loading at Low Temperature," 2016, Industrial Biotechnology, pp. 168-175, vol. 12, No. 3.

Harris et al., "Stimulation of Lignocellulosic Biomass Hydrolysis by Proteins of Glycoside Hydrolase Family 61: Structure and Function of a Large, Enigmatic Family," 2010, Biochemistry, pp. 3305-3316, vol. 49.

Hodge et al., "Soluble and insoluble solids contributions to high-solids enzymatic hydrolysis of lignocellulose," 2008, Bioresource Technology, pp. 8940-8948, vol. 99.

Huang et al., "Novel process for the coproduction of xylo-oligosaccharides, fermentable sugars, and lignosulfonates from hardwood," Bioresource Technology, 2016, pp. 600-607, vol. 219.

Iakovlev et al., "Kinetics of fractionation by SO2-ethanol-water (SEW) treatment: understanding the deconstruction of spruce wood chips," RSC Advances, 2012, pp. 3057-3068, vol. 2, No. 7.

Iakovlev et al., "SO2-ethanol-water (SEW) fractionation process: Production of dissolving pulp from spruce," Cellulose, 2014, pp. 1419-1429, vol. 21.

Karimi et al., "A critical review of analytical methods in pretreatment of lignocelluloses: Composition, imaging, and crystallinity," Bioresource Technology, 2016, pp. 1008-1018, vol. 200.

Keller et al., "Magnesium Bisulfite Pulping and Papermaking with Southern Pine," US Forest Service Research Paper, 1967.

Kilian, A., "Control of an acid sulphite batch pulp digester based on a fundamental process model,", Master Thesis, 1999, University of Pretoria.

Kumar et al., "Access of Cellulase to Cellulose and Lignin for Poplar Solids Produced by Leading Pretreatment Technologies," 2009, Biotechnol. Prog., pp. 807-819, vol. 25, No. 3.

Kumar et al., "Effects of Cellulase and Xylanase Enzymes on the Deconstruction of Solids from Pretreatment of Poplar by Leading Technologies," Biotechnol. Prog., 2009, pp. 302-314, vol. 25, No. 2.

Kumar et al., "Recent updates on different methods of pretreatment of lignocellulosic feedstocks: a review," Bioresour Bioprocess, 2017, vol. 4., No. 7.

Lan et al., "High titer ethanol production from SPORL-pretreated lodgepole pine by simultaneous enzymatic saccharification and combined fermentation," 2013, Bioresource Technology, pp. 291-297, vol. 127.

Leu et al., "Substrate-Related Factors Affecting Enzymatic Saccharification of Lignocelluloses; Our Recent Understanding," 2013, Bioenerg. Res., pp. 405-415, vol. 6.

Liu et al., "Multistep Process to Produce Fermentable Sugars and Lignosulfonates from Softwood Enzymolysis Residues," ACS Sustainable Chem. Eng., 2016, pp. 7225-7230, vol. 4.

Liu et al., "Effect of Sulfite Pretreatment to Overcome the Recalcitrance of Lignin (SPORL) on Enzymatic Saccharification of Corn Stalk," 2011, Bioresouces, 5001-5011, vol. 6(4).

Llano et al., "Detoxification of a Lignocellulosic Waste from a Pulp Mill to Enhance Its Fermentation Prospects", Energies, 2017, vol. 10, No. 348.

Mackie et al., "Effect of Sulphur Dioxide and Sulphuric Acid on Steam Explosion of Aspenwood," 1985, Journal of Wood Chemistry and Technology, pp. 405-425, vol. 5(3).

Mamers et al., "Explosion pretreatment of Pinus radiata woodchips for the production of fermentation substrates," 1984, Apita, pp. 644-649, vol. 37, No. 8.

Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.

Miles-Barrett et al., "Use of Bisulfite Processing to Generate Hight BO4 Content Water Soluble Lignosulfonates," ACS Sustainable Chem. Eng., 2017, pp. 1831-1839, vol. 5.

(56) References Cited

OTHER PUBLICATIONS

Monavari et al., "Improved One-Step Steam Pretreatment if S02-Impregnated Softwood with Time- Dependant Temperature Profile for Ethanol Production," 2010, Biotechnol. Prog., pp. 1054-1060, Vol.
Mupondwa et al., "Status of Canada's lignocellulosic ethanol: Part I: Pretreatment technologies," Renewable and Sustainable Energy Reviews, 2017, pp. 178-190, vol. 72.
Nguyen et al., "Dilute Acid Pretreatment of Softwoods," 1998, Applied Biochemistry and Biotechnology, pp. 77-89, vol. 70-72.
Nguyen et al., "Two-Stage Dilute Acid Pretreatment of Softwoods," 2000, Applied Biochemistry and Biotechnology, 561-576, vol. 84-86.
NREL, "Continual Shrinking-Bed Reactor Boosts Biomass Ethanol," Research Brief.
Ohgren et al., "Optimization of Steam Pretreatment of SO2-Impregnated Corn Stover for Fuel Ethanol Production," 2005, Applied Biochemistry and Biotechnology, pp. 1055-1067, vol. 121-124.
Pan et al., "Woody Biomass Sulfite Pretreatment to Overcome Lignocellulose Recalcitrance for Biofuel Production", Wisconsin Alumni Research Foundation.
Paulova et al., "Production of $2^{nd}$ Generation of Liquid Biofuels", Liquid Gaseous and Solid Biofuels—Conversion Techniques, 2013.
Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.
Rakkolainen et al., "SO2-Ethanol-Water Fractionation of Forest Biomass and Implications for Biofuel Production by Abe Fermentation," 2010, Cellulose Chem. Technol., pp. 139-145, vol. 44.
Ramos et al., "Characterization of Residual Lignin after SO2-Catalyzed Steam Explosion and Enzymatic Hydrolysis of Eucalyptus viminalis Wood Chips," 1999, J. Agric. Food Chem., pp. 2295-2302, vol. 47.
Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.
Ramos et al., "Effect of enzymatic hydrolysis on the morphology and fine structure of pretreated cellulosic residues," 1993, Enzyme Microb. Technol., pp. 821-831, vol. 15.
Ren et al., "Comparative Evaluation of Magnesium Bisulfite Pretreatment under Different pH Values for Enzymatic Hydrolysis of Corn Stover," Bioresources, 2016, pp. 7258-7270, vol. 11, No. 3.
Reknes, K., "The chemistry of lignosulphonate and the effect on performance of lignosulfonate base plasticizers and superplasticizers," $29^{th}$ Conference on Our World in Concrete & Structures, Aug. 2004, Singapore.
Rollin et al., "Increasing Cellulose Accessibility is More Important than Removing Lignin: A Comparison of Cellulose Solvent-Based Lignocellulose Fractionation and Soaking in Aqueous Ammonia," Biotechnology and Bioengineering, 2011, pp. 22-30, vol. 108. No. 1.
Sassner et al., "Steam Pretreatment of Salix with and without SO2 Impregnation for Production of Bioethanol," 2005, Applied Biochemistry and Biotechnology, pp. 1101-1117, vol. 121-124.
Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.
Schell et al., "Pretreatment of Softwood by Acid-Catalyzed Steam Explosion Followed by Alkali Extraction," 1998, Applied Biochemistry and Biotechnology, pp. 17-24, vol. 70-72.
Schwald et al., "Assessment of Pretreatment Conditions to Obtain Fast Complete Hydrolysis on High Substrate Concentrations," 1989, Applied Biochemistry and Biotechnology, pp. 29-44, vol. 20/21.

Selig et al., "The Effect of Lignin Removal by Alkaline Peroxide Pretreatment on the Susceptibility of Corn Stover to Purified Celluloytic and Xylanolytic Enzymes," Appl. Biochem. Biotechnol., 2009, pp. 397-406, Vo. 155.
Sendelius, "Steam Pretreatment Optimisation for Sugarcane Bagasse in Bioethanol Production," 2005, Master of Science Thesis, Lund University, Sweden.
Shahzad, M. A., "Effect of temperature and time on acid sulfite cooking for dissolving pulp," Degree Project, Karlstad University, 2012.
Shevchenko et al., "Optimization of monosaccharide recovery by post-hydrolysis of the water-soluble hemicellulose component after steam explosion of softwood chips," 2000, Bioresource Technology, pp. 207-211, vol. 72.
Shevchenko et al., "The Nature of Lignin from Steam Explosion/Enzymatic Hydrolysis of Softwood," 1999, Applied Biochemistry and Biotechnology, pp. 867-876, vol. 77-79.
Shi et al., "Sugar yields from dilute sulfuric acid and sulfur dioxide pretreatments and subsequent enzymatic hydrolysis of switchgrass," 2011, Bioresource Technology, pp. 8930-8938, vol. 102.
Shi et al., "Degradation Kinetics of Monosaccharides in Hydrochloric, Sulfuric, and Sulfurous Acid," Bioresources, 2012, pp. 4085-4097, vol. 7, No. 3.
Shi et al., "Pretreatment of Lignocellulosic Biomass", Beems Module B1.
Shuai et al., "Comparative study of SPORL and dilute-acid pretreatments of spruce for cellulosic ethanol production," 2010, Bioresource Technology, pp. 3106-3114, vol. 101.
Sipos et al., "Steam pretreatment of dry and ensiled industrial hemp for ethanol production," 2010, Biomass and Bioenergy, pp. 1-11.
Sixta, H., "Conventional Acid Sulfite Pulping," Aalto University, 2015.
Sluiter et al., "Determination of Structural Carbohydrates and Lignin in Biomass," NREL Technical Report 2012.
Soderstrom et al., "Effect of Washing on Yield in One- and Two-Step Steam Pretreatment of Softwood for Production of Ethanol," 2004, Biotechnol. Prog., pp. 744-749, vol. 20.
Soderstrom et al., "Separate versus Simultaneous Saccharification and Fermentation of Two-Step Steam Pretreated Softwood for Ethanol Production," 2005, Journal of Wood Chemistry, pp. 187-202, vol. 25.
Soderstrom et al., "Two-Step Steam Pretreatment of Softwood with SO2 Impregnation for Ethanol Production," 2002, Applied Biochemistry and Biotechnology, pp. 5-21, vol. 98-100.
Stenberg et al., "Optimisation of Steam Pretreatment of SO2-Impregnated Mixed Softwoods for Ethanol Production," 1998, J. Chem. Technol. Biotechnol, pp. 299-308, vol. 71.
Sumerskii et al., "Fast track for quantitative isolation of lignosulfonates from spent sulfite liquors," RSC Advances, 2015, pp. 92732-92742, vol. 5.
Szengyel et al., "Cellulase Production of Trichoderma reesei Rut C 30 Using Steam-Pretreated Spruce," 2000, Applied Biochemistry and Biotechnology, pp. 679-691, vol. 84-86.
Takahashi et al., "Removal of Acetic Acid from Spent Sulfite Liquor Using Anion Exchange Resin for Effective Xylose Fermentation with Pichia stipitis," Bioresources, 2013, pp. 2417-2428, vol. 8, No. 2.
Tao et al., "Process and technoeconomic analysis of leading pretreatment technologies for lignocellulosic ethanol production using switchgrass," 2011, Bioresource Technology, pp. 11105-11114, vol. 102.
Tengborg et al., "Comparison of SO2 and H2SO4 Impregnation of Softwood Prior to Steam Pretreatment on Ethanol Production," 1998, Applied Biochemistry and Biotechnology, pp. 3-15, vol. 70-72.
Tengborg et al., "Reduced inhibition of enzymatic hydrolysis of steam-pretreated softwood," 2001, Enzyme and Microbial Technology, pp. 835-844, vol. 28.
Thompson et al., "Chemical preconversion: application of low-severity pretreatment chemistries for commoditization of lignocellulosic feedstock," Biofuels, 2013, pp. 323-340, vol. 4, No. 3.

(56) References Cited

OTHER PUBLICATIONS

Tian et al., "Comparisons of SPORL and Dilute Acid Pretreatments for Sugar and Ethanol Productions from Aspen," 2011, Biotechnol. Prog. pp. 419-427, vol. 27, No. 2.

Tian et al., "Robust cellulosic ethanol production from SPORL-pretreated lodgepole pine using an adapted strain *Saccharomyces cerevisiae* without detoxification," 2010, Bioresource Technology, pp. 8678-8685, vol. 101.

Tian et al., "A comparison of various lignin-extraction methods to enhance the accessibility and ease of enzymatic hydrolysis of the cellulosic component of steam-pretreated poplar," Biotechnol. Biofuels, 2017, vol. 10, No. 157.

Trajano et al., "Fundamentals of Biomass Pretreatment at Low pH," 2013, Aqueous Pretreatment of Plant Biomass for Biological and Chemical Conversion to Fuels and Chemicals, pp. 103-128.

Vera et al., "Synergistic effects of mixing hybrid poplar and wheat straw biomass for bioconversion processes," 2015, Biotechnol Biofuels, pp. 1-10, vol. 8:226.

Vermaas et al., "Mechanism of lignin inhibition of enzymatic biomass deconstruction," Biotechnol Biofuels, 2015, vol. 8, No. 217.

Von Sivers et al., "A Techno-Economical Comparison of Three Processes for the Production of Ethanol from Pine," 1995, Bioresource Technology, pp. 43-52, vol. 51.

Wang et al., "Ethanol production from poplar wood through enzymatic saccharification and fermentation by dilute acid and SPORL pretreatments," 2012, Fuel, pp. 606-614, vol. 95.

Wang et al., "Influence of lignin addition on the enzymatic digestibility of pretreated lignocellulosic biomasses," Bioresource Technology, 2015, pp. 7-12, vol. 181.

Wang et al., "Lignosulfonate and elevated pH can enhance enzymatic saccharification of lignocelluloses," 2013, Biotechnology for Biofuels, pp. 1-10, vol. 6:9.

Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.

Wayman et al., "Hydrolysis of Biomass by Sulphur Dioxide," 1984, Biomass, pp. 183-191, vol. 6.

Wayman et al., "S02 Catalysed Prehydrolysis of Coniferous Wood for Ethanol Production," 1986, Biotechnology Letters, pp. 749-752, vol. 8, No. 10.

Wiman et al., "Cellulose accessibility determines the rate of enzymatic hydrolysis of steam-pretreated spruce," 2012, Bioresource Technology, pp. 208-215, vol. 126.

Wolfinger et al., "Modeling of the Acid Sulfite Pulping Process.—Problem Definition and Theoretical Approach for a Solution with the Main Focus on the Recovery of Cooking Chemicals," 2004, Lenzinger Berichte, pp. 35-45, vol. 83.

Wooley, Bob, "Production of 1,000 Gallons of BioJet," 2015, Presentation from 2015 Annual Meeting of Northwest Advanced Renewables Alliance (NARA).

Wyman et al., "Comparative data on effects of leading pretreatments and enzyme loadings and formulations on sugar yields from different switchgrass sources," 2011, Bioresource Technology.

Wyman et al., "Comparative Sugar Recovery and Fermentation Data Following Pretreatment of Poplar Wood by Leading Technologies," 2009, Biotechnol. Prog., pp. 333-339, vol. 25, No. 2.

You et al., "Kinetics of SO2-ethanol-water (AVAP) fractionation of sugarcane straw," Bioresource Technology, 2016, pp. 111-119, vol. 210.

Zhang et al., "Sulfite (SPORL) pretreatment of switchgrass for enzymatic saccharification," 2013, Bioresource Technology, pp. 127-134, vol. 129.

Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.

Zhou et al., "Comparisons of high titer ethanol production and lignosulfonate properties by SPORL pretreatment of lodgepole pine at two temperatures," RSC Advances, 2014, pp. 27030-27038, vol. 4.

Zhou et al., "High titer ethanol and lignosulfonate production from SPORL pretreated poplar at pilot scale," Frontier in Energy Research, 2015, vol. 3.

Zhu et al., "Case studies on sugar production from underutilized woody biomass using sulfite chemistry", Tappi Journal, 2015, pp. 577-583, vol. 14, No. 9.

Zhu et al., "Ethanol production from SPORL-pretreated lodgepole pine: preliminary evaluation of mass balance and process energy efficiency," 2010, Appl Microbiol Biotechnol, pp. 1355-1365, vol. 86.

Zhu et al., "High Titer Ethanol Production from Forest Residue Using Sulfite Mill Pulping Chemistry," 2015, Presentation at 2015 TAPPI IBBC.

Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.

Zhu et al., "On Polydispersity of Plant Biomass Recalcitrance and Its Effects on Pretreatment Optimization for Sugar Production," 2011, Bioenerg. Res., pp. 201-210, vol. 4.

Zhu et al., "Quantitative predictions of bioconversion of aspen by dilute acid and SPORL pretreatments using a unified combined hydrolysis factor (CHF)," 2012, Process Biochemistry, pp. 785-791, vol. 47.

Zhu et al., "Sulfite pretreatment (SPORL) for robust enzymatic saccharification of spruce and red pine," 2009, Bioresource Technology, pp. 2411-2418, vol. 100.

Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.

Zhu et al., "Woody biomass pretreatment for cellulosic ethanol production: Technology and energy consumption evaluation," 2010, Bioresource Technology, pp. 4992-5002, vol. 101.

International Search Report and Written Opinion dated Feb. 21, 2019 for PCT Application No. PCT/CA2018/000213, filed Nov. 9, 2018.

International Search Report and Written Opinion dated Mar. 8, 2019 for PCT Application No. PCT/CA2018/000217, filed Nov. 9, 2018.

Office Action for U.S. Appl. No. 17/040,738 dated Jun. 3, 2021, in 30 pages.

Office Action for U.S. Appl. No. 16/761,180 dated Jun. 24, 2021, in 25 pages.

Rodsrud et al., "History and future of world's most advanced biorefinery in operation", Biomass and Bioenergy, 2012, vol. 46, pp. 46-59.

Gratzel et al., "Chemistry of Pulping: lignin reactions." American Chemical Society Symposium Series, 2000, vol. Ch. 20, pp. p. 3932-421.

Yan et al., "Influence of pH on the behaviour of lignosulfonate macromolecules in aqueous solution". Colloids and Surfaces: A Physiochemical and Engineering aspects, Nov. 1, 2010 (Jan. 11, 2010), vol. 37 (1) pp. p. 50-58.

Gellerstedt et al., "Towards a new concept of lignin condensation in Kraft pulping" C.R. Biologies, 2004, vol. 327.

Andritz, "BioFuel Equipment—derived from Pulp and Fiberboard applications for Ligno-Cellulosic BioFuel & BioChemicals Technology" 2012.

McElroy "Not so run of the Mill", Biomassmagazine, http://biomassmagazine.com/articles/1297/not-so-run-of-the-mill.

Philips, et al., "Integration of pulp and paper technology with bioethanol production", Biotechnology for Biofuels 2013 6:13.

Zhu et al., "Applications of lignin-derived catalysts for green synthesis", Green Energy & Environment, https://doi.org/10.1016/i.gee.2019.01.003.

International Search Report and Written Opinion dated May 3, 2019 for PCT Application No. PCT/CA2018/000215, filed Nov. 9, 2018.

\* cited by examiner

LOW TEMPERATURE PRETREATMENT WITH SULFUR DIOXIDE

CROSS-REFERENCE TO RELATED APPLICATIONS

This application claims the priority benefit of U.S. Provisional application No. 62/583,705, filed Nov. 9, 2017, and U.S. Provisional application No. 62/725,583 filed Aug. 31, 2018, each of which is incorporated herein by reference.

TECHNICAL FIELD

The present disclosure relates generally to a process and/or system for converting lignocellulosic biomass to a fuel, where the lignocellulosic biomass is pretreated with sulfur dioxide, and optionally bisulfite salt, at relatively low temperature prior to enzymatic hydrolysis.

BACKGROUND

Lignocellulosic biomass refers to plant biomass that includes cellulose, hemicellulose, and lignin. Lignocellulosic biomass may be used to produce biofuels (e.g., ethanol, butanol, methane) by breaking down cellulose and/or hemicellulose into their corresponding monomers (e.g., sugars), which can then be converted to the biofuel via microorganisms. For example, glucose can be fermented to produce an alcohol such as ethanol or butanol.

While lignocellulosic biomass can be broken down into sugars solely using various chemical processes (e.g., acid hydrolysis), enzymatic hydrolysis is often the preferred approach for generating glucose from cellulose as it is associated with higher yields, higher selectivity, lower energy costs, and milder operating conditions. However, as a result of the complicated structure of the plant cell wall, the enzymatic digestibility of cellulose in native lignocellulosic biomass is often low unless a large excess of enzyme is used (e.g., lignocellulosic biomass may be considered recalcitrant to biodegradation).

In order to reduce biomass recalcitrance (e.g., open up the structure of the lignocellulosic material, make the cellulose more accessible to the enzymes, and/or generally improve enzymatic digestibility of the cellulose) lignocellulosic biomass may be pretreated, a process which can reduce the amount of enzyme and/or enzymatic hydrolysis time required to convert the cellulose to glucose. For example, pretreatment may affect the hemicellulose-lignin sheathing that encases the cellulose.

Pretreatments such as dilute acid or steam explosion may promote hemicellulose dissolution. However, when process conditions for dilute acid or steam explosion are severe, the hemicellulose may degrade to compounds that are potentially inhibitory to enzymatic hydrolysis. In addition, such processes may result in acid-catalyzed condensation of lignin.

Pretreatments such as alkali, organic solvent (organosolv), or aqueous ammonia may promote lignin dissolution. However, such processes may compromise the recovery of the hemicellulose component or may be relatively expensive (e.g., relative to dilute acid processes). For example, with regard to organsolv type pretreatments, the cost of solvent, the additional steps of removing and/or recovering the solvent (e.g., many organic solvents are potentially inhibiting to enzymes), and/or the potential fire and explosion hazards related to the solvent, may increase the cost of such processes.

Pretreatments based on modified sulfite pulping have been proposed. In previous sulfite-pulping type pretreatments, lignin dissolution has been found to increase with increasing pH and/or increasing sulfite concentration, while hemicellulose dissolution has been found to decrease with increasing pH. For example, In U.S. Pat. No. 9,243,364, Zhu et al. disclose a two stage process including a first stage, where the lignocellulosic biomass is subjected to a bisulfite cook where the pH>3 (e.g., a neutral bisulfite cook) to promote delignification and lignin sulfonation, and a second stage, where the pH of the solution is decreased (e.g., to a pH between 1 and 3 by adding $H_2SO_4$) in order to promote the depolymerization and dissolution of hemicelluloses.

SUMMARY

According to one aspect of the invention there is provided a process for producing a fuel from lignocellulosic biomass comprising: (a) obtaining a feedstock comprising lignocellulosic biomass; (b) feeding said feedstock and sulfur dioxide into a pretreatment reactor, wherein a total amount of sulfur dioxide in the pretreatment reactor is greater than 70 wt % based on dry weight lignocellulosic biomass; (c) heating the feedstock and sulfur dioxide in the pretreatment reactor at one or more temperatures between 110° C. and 150° C. for more than 60 minutes; (d) obtaining a slurry of pretreated material produced from (c), said slurry having a solid fraction comprising cellulose and a liquid fraction comprising solubilized hemicellulose; (e) hydrolyzing cellulose in the solid fraction to glucose, said hydrolyzing comprising adding cellulase to at least the solid fraction; (f) fermenting the glucose to a fermentation product, said fermenting comprising adding a microorganism to at least the glucose; and (g) recovering the fermentation product, wherein said fuel comprises the fermentation product.

According to one aspect of the invention there is provided a process for producing a fuel from lignocellulosic biomass comprising: (a) obtaining a feedstock comprising lignocellulosic biomass; (b) feeding said feedstock and sulfur dioxide into a pretreatment reactor, wherein a total amount of sulfur dioxide in the pretreatment reactor is sufficient to provide an initial pH that is less than 1.25 measured at ambient temperature; (c) heating the feedstock and sulfur dioxide in the pretreatment reactor at one or more temperatures between 110° C. and 150° C. for more than 60 minutes; (d) obtaining a slurry of pretreated material produced from (c), said slurry having a solid fraction comprising cellulose and a liquid fraction comprising solubilized hemicellulose; (e) hydrolyzing cellulose in the solid fraction to glucose, said hydrolyzing comprising adding cellulase to at least the solid fraction; (f) fermenting the glucose to a fermentation product, said fermenting comprising adding a microorganism to at least the glucose; and (g) recovering the fermentation product, wherein the fuel comprises the fermentation product.

DETAILED DESCRIPTION

Figure 1:
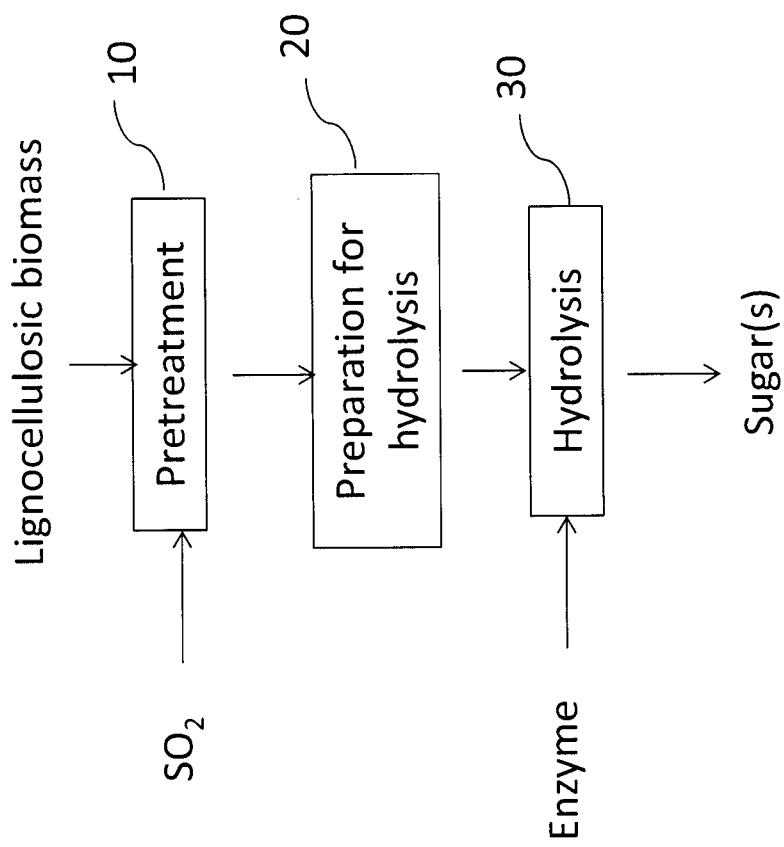
FIG. 1 is a block flow diagram of a method according to one embodiment of the invention.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a", "an," and "the" may include plural references unless the context clearly dictates otherwise. The terms "comprises", "comprising", "including", and/or "includes", as used herein, are intended to mean "including but not limited to". The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, those skilled in the art will understand that the order of addition is not critical (unless stated otherwise).

The instant disclosure describes a process wherein lignocellulosic biomass is pretreated with sulfur dioxide, and optionally bisulfite salt, prior to enzymatic hydrolysis. By providing a relatively high $SO_2$ concentration (e.g., greater than 70 wt % on dry lignocellulosic biomass), enzymatic hydrolysis can be improved even when the pretreatment is conducted as a single stage pretreatment and/or when the pretreatment does not use a solvent for lignin (e.g., ethanol). Advantageously, this single stage pretreatment can provide both good hemicellulose dissolution and good lignin dissolution.

Referring to FIG. 1, there is shown a method in accordance with one embodiment of the invention. Lignocellulosic biomass is subjected to a pretreatment 10 (e.g., an $SO_2$ pretreatment), which includes heating the lignocellulosic biomass in the presence of $SO_2$ at a temperature between about 110° C. and about 150° C. for more than about 60 minutes. During this heating step the $SO_2$ is present in a relatively high amount (e.g., $SO_2$ concentration that is greater than about 70 wt % based on dry weight of incoming lignocellulosic biomass). The pretreated material is then prepared 20 for hydrolysis (e.g., flashed, filtered, washed, cooled, and/or pH adjusted) and at least the solid fraction thereof is hydrolyzed 30 with added enzyme. The hydrolysis 30 produces sugar (e.g., the cellulose in the pretreated material is converted to glucose). Optionally, the glucose produced during the hydrolysis 30 is fermented (e.g., as part of a separate fermentation step or as part of a simultaneous hydrolysis/fermentation). For example, in one embodiment, the glucose is fermented to an alcohol (e.g., ethanol or butanol), which may be recovered in an alcohol recovery step. In one embodiment, the glucose from the hydrolysis 30 is fermented to ethanol using yeast (*Saccharomyces cerevisiae*). In one embodiment, the glucose from hydrolysis 30 is fermented along with C5 sugar derived from pretreatment using a microbe that can ferment both C6 and C5 sugars.

Feedstock

In one embodiment, the feedstock includes lignocellulosic biomass (e.g., that needs to be pretreated in order to improve enzymatic digestibility). Lignocellulosic biomass may refer to any type of biomass containing cellulose, hemicellulose, and lignin. In one embodiment, the lignocellulosic biomass has a combined content of cellulose, hemicellulose, and lignin that is greater than 25 wt %, greater than 50 wt %, or greater than 75 wt %. In one embodiment, sucrose, fructose, and/or starch are also present, but in lesser amounts than cellulose and hemicellulose.

In one embodiment, the feedstock includes: (i) energy crops; (ii) residues, byproducts, or waste from the processing of plant biomass in a facility or feedstock derived therefrom; (iii) agricultural residues; (iv) forestry biomass; and/or (v) waste material derived from a pulp and paper process.

Energy crops include biomass crops such as grasses, including C4 grasses, such as switch grass, energy cane, sorghum, cord grass, rye grass, miscanthus, reed canary grass, C3 grasses such as *Arundo donax*, or a combination thereof.

Residues, byproducts, or waste from the processing of plant biomass include residues remaining after obtaining sugar from plant biomass (e.g., sugar cane bagasse, sugar cane tops and leaves, beet pulp, Jerusalem artichoke residue), and residues remaining after grain processing (e.g., corn fiber, corn stover, and bran from grains). Agricultural residues include, but are not limited to soybean stover, corn stover, sorghum stover, rice straw, sugar cane tops and/or leaves, rice hulls, barley straw, wheat straw, canola straw, oat straw, oat hulls, corn fiber, and corn cobs.

Forestry biomass and/or waste material derived from a pulp and paper process includes hardwood, softwood, recycled wood pulp fiber, woodchips, wood pellets, sawdust, trimmings, hog fuel, bark, fines, and/or slash from logging operations.

In one embodiment, the feedstock is an energy or biomass crop. In one embodiment, the feedstock comprises an agricultural residue. In one embodiment, the feedstock comprises a non-woody feedstock. In one embodiment, the feedstock comprises hardwood. In one embodiment, the feedstock comprises softwood. In one embodiment, the feedstock includes bagasse. In one embodiment, the feedstock comprises wheat straw, or another straw. In one embodiment, the feedstock comprises stover. In one embodiment, the feedstock is a mixture of fibers that originate from different kinds of plant materials, including mixtures of cellulosic and non-cellulosic feedstock. In one embodiment, the feedstock is a second generation feedstock.

Feedstock Preparation

In one embodiment, the feedstock is subjected to one or more optional preparatory steps prior to the pretreatment and/or as part of the pretreatment. Some examples of these optional preparatory steps include size reduction, washing, leaching, sand removal, soaking, wetting, slurry formation, dewatering, plug formation, addition of heat, and addition of chemicals (e.g., pretreatment and/or other). In general, these preparatory steps may depend on the type of biomass and/or the selected pretreatment conditions.

In one embodiment, the feedstock is subjected to a size reduction. Some examples of size reduction methods include milling, grinding, agitation, shredding, compression/expansion, and/or other types of mechanical action. Size reduction by mechanical action may be performed by any type of equipment adapted for the purpose, for example, but not limited to, hammer mills, tub-grinders, roll presses, refiners, hydropulpers, and hydrapulpers. In one embodiment, feedstock includes agricultural residue and is subject to a size reduction to yield an average length between about 1/16 inch and about 6 inches. In one embodiment, feedstock includes a woody feedstock and is subject to a size reduction to yield woodchips having an average thickness that is less than 3 cm, less than 2 cm, less than 1.5 cm, less than 1.25 cm, less than 1 cm, less than 0.8 cm, or less than 0.6 cm.

In one embodiment, the feedstock is washed and/or leached with a liquid (e.g., water and/or an aqueous solution). Washing, which may be performed before, during, or after size reduction, may remove sand, grit, fine particles of the feedstock, and/or other foreign particles that otherwise may cause damage to the downstream equipment. Leaching, which may be performed before, during, or after size reduction, may remove soluble components from the feedstock. Leaching may remove salts and/or buffering agents.

In one embodiment, the feedstock is subject to sand removal. For example, in one embodiment, the feedstock is washed to remove sand. Alternatively, or additionally, sand may be removed using other wet or dry sand removal techniques that are known in the art (e.g., including the use of a hydrocyclone or a sieve).

In one embodiment, the feedstock is slurried in liquid (e.g., water), which allows the feedstock to be pumped. In one embodiment, the feedstock is slurried subsequent to size reduction, washing, and/or leaching. The desired weight ratio of water to dry biomass solids in the slurry may be determined by factors such as pumpability, pipe-line requirements, and other practical considerations. In general, slurries having a consistency less than about 10 wt % may be pumped using a relatively inexpensive slurry pump.

In one embodiment, the feedstock is soaked in water and/or an aqueous solution (e.g., comprising a pretreatment chemical). Soaking the feedstock may allow pretreatment chemical(s) to more uniformly impregnate the biomass, which in turn may provide even cooking in the heating step of pretreatment. For example, soaking the feedstock in a solution comprising a pretreatment chemical (e.g., such as sulfuric acid and/or sulfurous acid) typically provides uniform impregnation of the biomass with the pretreatment chemical. Soaking the feedstock in water, may allow gaseous pretreatment chemicals (e.g., sulfur dioxide) to more uniformly and/or completely impregnate the lignocellulosic biomass during subsequent chemical addition steps. In general, soaking may be carried out at any suitable temperature and/or for any suitable duration.

In one embodiment, the feedstock is wet with a liquid (e.g., water or an aqueous solution) or steam in order to moisten the lignocellulosic biomass and provide a desired consistency. In general, the term consistency refers to the amount of undissolved dry solids or "UDS" in a sample, and is often expressed as a ratio on a weight basis (wt:wt), or as a percent on a weight basis, for example, % (w/w), also denoted herein as wt %. For example, consistency may be determined by filtering and washing the sample to remove dissolved solids and then drying the sample at a temperature and for a period of time that is sufficient to remove water from the sample, but does not result in thermal degradation of the sample. The dry solids are weighed. The weight of water in the sample is the difference between the weight of the wet sample and the weight of the dry solids.

In one embodiment, the feedstock is at least partially dewatered (e.g., to provide a specific consistency). In one embodiment, the feedstock is at least partially dewatered in order to remove at least some of the liquid introduced during washing, leaching, slurrying, and/or soaking. In one embodiment, dewatering is achieved using a drainer, filtration device, screen, screw press, and/or extruder. In one embodiment, dewatering is achieved using a centrifuge. In one embodiment, the dewatering is achieved prior to and/or as part of plug formation. Some examples of plug formation devices that dewater biomass include a plug screw feeder, a pressurized screw press, a co-axial piston screw feeder, and a modular screw device.

Pretreatment

In one embodiment, the pretreatment includes subjecting the feedstock to a pretreatment with sulfur dioxide. Sulfur dioxide ($SO_2$) is a gas, which when dissolved in water, may be also referred to as sulfurous acid ($H_2SO_3$). The term "pretreating" or "pretreatment", as used herein, refers to one or more steps where the feedstock is treated to improve the enzymatic digestibility thereof (e.g., where the structure of the lignocellulosic biomass is disrupted such that the cellulose in the lignocellulosic biomass is more susceptible and/or accessible to enzymes in a subsequent hydrolysis).

In one embodiment, the pretreatment includes an "$SO_2$ pretreatment". The term "$SO_2$ pretreatment", as used herein, refers to an acid pretreatment wherein the lignocellulosic biomass is in contact with $SO_2$, and wherein to the extent any alkali is added for the pretreatment it is added in an amount that is less than 0.5 wt % (based on dry weight of incoming lignocellulosic biomass), to the extent any organic solvent is added for the pretreatment it is added in an amount that is less than 5 wt % (based on dry weight of incoming lignocellulosic biomass), and to the extent any carbonyl compound (or precursor) is added to form α-hydroxysulfonic acid for the pretreatment it is added in an amount less than 0.5 wt % (based on dry weight of incoming lignocellulosic biomass).

In one embodiment, the pretreatment includes pretreating the lignocellulosic biomass in the presence of $SO_2$ and bisulfite salt (e.g., $HSO_3^-$ salts). As the pretreatment is conducted in the presence of bisulfite salt and $SO_2$, at low pH values (i.e., below 2), it may be referred to as an acid bisulfite pretreatment. The bisulfite salts, which for example may have $Na^+$, $Ca^{2+}$, $K^+$, $Mg^{2+}$, or $NH_4^+$ counter ions, may be added directly (e.g., added as $NaHSO_3$) and/or may be formed in solution (e.g., by introducing the $SO_2$ into a solution containing alkali (e.g., a NaOH solution), by adding alkali into a sulfurous acid solution, or by adding sulfite salts to an aqueous $SO_2$ solution).

In one embodiment, the pretreatment includes a pretreatment wherein the lignocellulosic biomass is treated with $SO_2$ and lignosulfonic acid. The lignosulfonic acid may be generated in situ and/or may be added. Added lignosulfonic acid may be obtained commercially or may be a by-product of the pretreatment process. For example, in one embodiment, the added lignosulfonic acid is introduced into pretreatment when a portion of the pretreated biomass is redirected back to the pretreatment (e.g., as a slip stream). In one embodiment, the lignosulfonic acid is obtained by desalinating a lignosulfonate. For example, in one embodiment, a lignosulfonate produced by the process is contacted with a cation exchange resin to remove cations and recycled back to pretreatment.

In one embodiment, the pretreatment is conducted at a relatively low temperature. In one embodiment, the pretreatment includes heating the lignocellulosic biomass with $SO_2$ at one or more temperatures between about 110° C. and about 160° C. In one embodiment, the pretreatment includes heating the lignocellulosic biomass with $SO_2$ at one or more temperatures between about 110° C. and about 150° C. In one embodiment, the pretreatment includes heating the lignocellulosic biomass with $SO_2$ at one or more temperatures below 150° C. and greater than 120° C., greater than 125° C., greater than 130° C., greater than 135° C., or greater than 140° C. Using pretreatment temperatures between about 110° C. and about 150° C. advantageously avoids the equipment and/or xylose degradation associated with pretreatments at relatively high temperatures (e.g., greater than 160° C.).

In one embodiment, the pretreatment time and/or total amount of $SO_2$ is selected to convert most of the hemicellulose component to soluble sugars (e.g., xylose, mannose, arabinose, and glucose), but little of the cellulose component to sugars (e.g., which may be hydrolyzed in a subsequent enzymatic hydrolysis). For example, in one embodiment, the degree of pretreatment is selected such that the amount of xylan hydrolyzed to xylose is greater than about 50 wt %, about 60 wt %, about 70 wt %, about 80 wt %, or about 90 wt %.

In one embodiment, the pretreatment time and/or total amount of $SO_2$ provided is selected to provide a pretreatment severity that improves enzyme digestibility of the lignocellulosic biomass. For example, it has been found that when the pretreatment temperature is 130° C., and the total amount of $SO_2$ is between 20 wt % and 45 wt % based on dry weight of lignocellulosic biomass, that enzymatic digestibility of wheat straw is substantially improved when the pretreatment time is greater than 120 minutes, and significantly improved when the pretreatment time is greater than 180 minutes. When the total amount of $SO_2$ is about 74 wt % based on dry weight of lignocellulosic biomass, the enzymatic digestibility of wheat straw has been found to be good when the pretreatment time is 180 minutes. In general, providing a pretreatment time that is at least 90 minutes and a total amount of sulfur dioxide that is at least about 25 wt % based on dry weight of lignocellulosic biomass has been shown to provide good hydrolysis for both wheat straw and bagasse that are washed with water after pretreatment.

The term "total amount of $SO_2$", as used herein, refers to the total amount of $SO_2$ provided for the pretreatment per amount of lignocellulosic biomass on a dry weight basis. In general, the "total amount of $SO_2$" may be calculated from the grams of $SO_2$ present initially per gram of dry weight of lignocellulosic biomass present (e.g., as a weight percentage (wt %)). For example, if 25 g of gaseous $SO_2$ is added to 100 g of lignocellulosic biomass having total solids (TS) content of 93.25% (e.g., 6.75% moisture content), the total amount of $SO_2$ is calculated as follows:

$$\text{Total amount of SO2} = \frac{\text{g SO2 added}}{\text{g biomass added} * TS \text{ content}} = \frac{25 \text{ g SO2}}{(100 \text{ g biomass}) * 0.9325} = 27 \text{ wt \%}$$

Alternatively, if 52 mL of sulfurous acid prepared to be about 6% (w/w) $H_2SO_3$ is added to 6.43 g of lignocellulosic biomass having a total solids (TS) content of 93.25% (e.g., 6.75% moisture content), the total amount of $SO_2$ is calculated as:

$$\text{Total amount of SO2} = \frac{\text{g SO2 added}}{\text{g biomass added} * TS \text{ content}}$$

$$= \frac{\text{volume H2SO3 (mL) added} * \text{density of H2SO3} \left(\frac{g}{mL}\right) * \frac{6 \text{ g}}{100 \text{ g}} * \frac{Mw \text{ SO2}}{Mw \text{ H2SO3}}}{\text{g biomass added} * TS \text{ content}}$$

$$= \frac{52 * 1.03 * 6 * 64.066/(100 * 82.07)}{6.43 * 0.9325}$$

$$= 42 \text{ wt \%}$$

In some cases, the total amount of $SO_2$ can be represented by the $SO_2$ loading. The term "$SO_2$ loading" is often used for continuous systems, where it refers to the amount of $SO_2$ fed to the pretreatment system per amount of dry lignocellulosic biomass fed to the pretreatment system (e.g., calculated from the grams of $SO_2$ provided per gram of dry weight lignocellulosic biomass (e.g., as a weight percentage (wt %)). However, in some cases, the total amount of $SO_2$ can be higher than the $SO_2$ loading (e.g., if some $SO_2$ is held within the pretreatment system when the pretreated lignocellulosic biomass is discharged). For example, in PCT Application No. PCT/CA2016/051089, filed on Sep. 16, 2016, a pretreatment system having a charge of $SO_2$ is disclosed. In this case, the total amount of $SO_2$ provided includes the amount of $SO_2$ provided in the charge of $SO_2$.

In some cases, the concentration of $SO_2$ may include contributions from bisulfate salts added to the pretreatment. In general, the $SO_2$ in the pretreatment may be present as $SO_2$, $H_2SO_3$, $HSO_3^-$, and/or $SO_3^{2-}$, according to the following reactions:

$$SO_2 + H_2O \Longleftrightarrow H_2SO_3 \qquad (1)$$

$$H_2SO_3 + H_2O \Longleftrightarrow HSO_3^- + H_3O^+ \qquad (2)$$

$$HSO_3^- + H_2O \Longleftrightarrow SO_3^{2-} + H_3O^+ \qquad (3)$$

However, at the conditions used in the pretreatment (e.g., pH values less than about 1.3), the equilibrium in equation (3) will be shifted to the left and there will be negligible contributions from $SO_3^{2-}$.

In any case, the "concentration of $SO_2$" or "$SO_2$ concentration" in pretreatment, which takes into account contributions from $SO_2$, $H_2SO_3$, $HSO_3^-$, and $SO_3^{2-}$, can be expressed on a molar-equivalent-to-$SO_2$ basis, as weight percent $SO_2$. The weight percent of $SO_2$ may be based on the total pretreatment liquid weight (on liquor), or based on the dry lignocellulosic biomass weight (on dry solids). The total pretreatment liquid weight includes the weight of moisture in the feedstock, but not the weight of the dry solids.

In one embodiment, the pretreatment includes contacting the lignocellulosic biomass with $SO_2$ at one or more temperatures between about 110° C. and about 150° C., for more than about 90 minutes, where the total amount of $SO_2$ is greater than 35 wt % or greater than 50 wt % (i.e., w/w based on dry weight of lignocellulosic biomass).

In one embodiment, the pretreatment includes contacting the lignocellulosic biomass with $SO_2$ at one or more temperatures between about 110° C. and about 150° C., for more than about 60 minutes, where the total amount of $SO_2$ is greater than 70 wt % (i.e., w/w based on dry weight lignocellulosic biomass).

In one embodiment, the pretreatment includes contacting the lignocellulosic biomass with $SO_2$ at one or more temperatures between about 120° C. and about 150° C., for more than about 60 minutes, where the $SO_2$ concentration is greater than 60 wt %, greater than 65 wt %, greater than 70 wt %, greater than 75 wt %, greater than 80 wt %, greater than 85 wt %, greater than 90 wt %, greater than 95 wt %, or greater than 100 wt % (i.e., w/w based on dry weight lignocellulosic biomass).

In one embodiment, pretreatment includes contacting the lignocellulosic biomass with $SO_2$ at one or more temperatures between about 110° C. and about 150° C., for a time sufficient to solubilize at least 50 wt %, at least 55 wt %, at least 60 wt %, at least 65 wt %, at least 70 wt %, at least 75 wt %, or at least 80 wt % of the lignin initially present in the lignocellulosic biomass. In one embodiment, pretreatment includes contacting the lignocellulosic biomass with $SO_2$ at one or more temperatures between about 110° C. and about 150° C., for a time sufficient to solubilize at least 80 wt %, at least 85 wt %, at least 90 wt %, or at least 95 wt % of the hemicellulose initially present the lignocellulosic biomass.

In one embodiment, the pretreatment includes contacting the lignocellulosic biomass with $SO_2$ at one or more temperatures between about 110° C. and about 150° C., for more than about 180 minutes, where the total amount of $SO_2$ is greater than 20 wt % and less than 100 wt %, based on dry weight lignocellulosic biomass.

Surprisingly, it has been found that the glucose yield achieved with enzymatic hydrolysis after an $SO_2$ pretreatment conducted at about 130° C. can be similar to that achieved after a high temperature $SO_2$ pretreatment (e.g., at 230° C., 21 wt % $SO_2$, 3.7 minutes, 10 wt % consistency) and/or better than that achieved after a high temperature $H_2SO_4$-catalyzed steam pretreatment (e.g., at 200° C., 1.26 wt % $H_2SO_4$, 2 minutes, 30 wt % consistency).

Without being bound by theory, this high glucose yield after enzymatic hydrolysis is attributed to the fact that the low temperature $SO_2$ pretreatment (e.g., at 130° C.), which is an acid pretreatment, can target dissolution of both hemicellulose and lignin when a relatively high amount of total $SO_2$ and/or long pretreatment time is used.

For example, it has been found that by increasing the total amount of $SO_2$ in $SO_2$ pretreatment (e.g., greater than 20 wt % based on dry weight of lignocellulosic biomass) and/or by increasing the pretreatment time (e.g., greater than 90 minutes) the amount of lignin solubilized can exceed 50% without having to add the amount of alkali associated with sulfite pulping based pretreatment and/or without having to add significant amounts of organic solvent to facilitate lignin removal. In addition, it has been found that by increasing the total amount of sulfur dioxide in $SO_2$ pretreatment (e.g., greater than 20 wt % based on dry weight of lignocellulosic biomass) and/or by increasing the pretreatment time (e.g., greater than 90 minutes) the amount of xylose produced can reach over 80%.

More surprisingly, it has been found that by increasing the total amount of $SO_2$ in $SO_2$ pretreatment (e.g., greater than 20 wt % based on dry weight of lignocellulosic biomass) and/or by increasing the pretreatment time (e.g., greater than 90 minutes), the glucose yield at 72 hours of enzymatic hydrolysis can be higher than 80%, while the glucose yield at 96 hours of enzymatic hydrolysis can be higher than 90%, with only 5 mg/g (5 milligrams protein per gram cellulose) of enzyme (i.e., for wheat straw). This is surprising because low temperature $H_2SO_4$ pretreatment does not provide the same increase in enzymatic digestibility, and because it has been previously believed that it was important to bond $SO_2$ to significant amounts of other compounds (e.g., carbonyl compounds) in order to facilitate low temperature pretreatments (α-hydroxysulfonic acid pretreatment).

As discussed above, the low temperature $SO_2$ pretreatment disclosed herein can provide good lignin solubilization, good hemicellulose hydrolysis, and good glucose yield without having to add the amount of alkali associated with sulfite pulping based pretreatments and/or without having to add an amount of organic solvent associated with an organosolv process (e.g., to facilitate lignin removal).

It has also been found that pretreating lignocellulosic biomass with $SO_2$ at high $SO_2$ concentrations (e.g., greater than 70 wt % (on dry solids)) can be advantageous when sulfite salt is present (e.g., when alkali is added).

Sulfite salts may, for example, be formed by reacting an alkali (base) with aqueous $SO_2$, or by bubbling $SO_2$ into a solution containing alkali (base). For example, consider the following acid-base reaction:

$$H_2SO_3 + MOH \Longleftrightarrow MHSO_3 + H_2O \qquad (4)$$

where M may be referred to as the counter cation. Some examples of alkali suitable for use providing the bisulfite salt include NaOH, $NaHCO_3$, $Na_2CO_3$, KOH, $KHCO_3$, $K_2CO_3$, $CaCO_3$, MgO, $NH_3$, etc.

In one embodiment, an aqueous pretreatment liquor is prepared by adding $SO_2$ and/or alkali. In general, the alkali may include any compound(s) that forms the desired bisulfite salt when $SO_2$ is present (e.g., $NaHSO_3$, $KHSO_3$, $Ca(HSO_3)_2$, $Mg(HSO_3)_2$, or $(NH_4)HSO_3$). In one embodiment, the alkali includes NaOH, $NaHCO_3$, $Na_2CO_3$, KOH, $KHCO_3$, $K_2CO_3$, $CaCO_3$, CaO, MgO, or $NH_3$. In one embodiment, the alkali is NaOH, CaO, MgO, or $NH_4OH$.

The amount of alkali added (e.g., NaOH or CaO) can be expressed as the weight of alkali per dry weight of lignocellulosic solids (on dry solids). For example, if 0.4 g of NaOH is added to 100 g of lignocellulosic biomass having total solids (TS) content of 93.25% (e.g., 6.75% moisture content), the amount of alkali added is calculated as:

$$\text{Amount of alkali added} = \frac{\text{g alkali added}}{\text{g biomass added} * TS \text{ content}} =$$

$$\frac{0.4 \text{ g}}{(100 \text{ g biomass}) * 0.9325} = 0.43 \text{ wt \% on dry solids}$$

As the alkali may be provided as a hydroxide, carbonate salt, or other form, for comparative purposes, the "concentration of alkali" or "alkali concentration" may be expressed on a molar-equivalent-to-M basis, where M is the cation on a monovalent basis ($Na^+$, $K^+$, $NH_4^+$, $\frac{1}{2}Ca^{2+}$, $\frac{1}{2}Mg^{2+}$), but expressed as weight percent hydroxide (OH).

In one embodiment, the amount of alkali added will be less than about 0.5 wt % based on dry weight of lignocellulosic biomass. In one embodiment, the amount of alkali added for pretreatment is less than 0.4 wt % or less than 0.25 wt % (on dry solids). In one embodiment the amount of alkali added for pretreatment corresponds to a bisulfite loading that is less than 1 wt % or less than 0.5 wt % (on dry solids). In one embodiment, the amount of bisulfite salt formed for pretreatment is less than 2 wt %, or less than 1 wt % (on dry solids).

In one embodiment, sufficient alkali is added to provide an alkali concentration, near the start of pretreatment, that is at least about 0.05 wt %, at least about 0.1 wt %, at least about 0.2 wt %, at least about 0.3 wt %, at least about 0.4 wt %, or at least about 0.5 wt %, each expressed as weight percent hydroxide on liquor (e.g., OH, on liquor). In one embodiment, sufficient alkali is added to provide an alkali concentration that is between about 0.01 wt % (OH, on liquor) and about 0.7 wt % (OH, on liquor). In one embodiment, sufficient alkali is added to provide an alkali concentration that is between about 0.05 wt % (OH, on liquor) and about 0.5 wt % (OH, on liquor). In one embodiment, sufficient alkali is added to provide an alkali concentration that is between about 0.1 wt % (OH, on liquor) and about 0.3 wt % (OH, on liquor). In one embodiment, sufficient alkali is added to provide an alkali concentration, near the start of pretreatment, between about 0 wt % and less than about 0.42 wt % (OH, on liquor).

The alkali concentration on liquor may be converted to the alkali on dry solids by taking the solids consistency into account. In one embodiment, sufficient alkali is added to provide an alkali concentration, near the start of pretreatment, that is at least about 0.10 wt %, at least about 0.5 wt %, at least about at least about 1 wt %, at least about 1.5 wt %, at least about 2 wt %, at least about 2.5 wt %, at least about 3 wt %, at least about 3.5 wt %, at least about 4 wt %, at least about 5 wt %, or at least about 6 wt %, each expressed as weight percent hydroxide on dry solids (e.g., OH, on dry solids). In one embodiment, sufficient alkali is added to provide an alkali concentration, near the start of pretreatment, between about 0.50 wt % and about 3 wt % (OH, on dry solids).

For reference, if alkali is provided only by adding NaOH, an alkali concentration of about 0.16 wt % (OH, on liquor) may be roughly equivalent to a NaOH charge of about 0.38 wt % (on liquor) or a $NaHSO_3$ charge of about 1 wt % (on liquor). A $NaHSO_3$ charge of about 1 wt % (on liquor) corresponds to a $NaHSO_3$ charge of about 9 wt % (on dry solids) when the consistency is about 10 wt %, about 4 wt % (on dry solids) when the consistency is about 20 wt %, or about 1.5 wt % (on dry solids) when the consistency is about 40 wt %.

The alkali concentration in the aqueous pretreatment liquor may include contributions from alkali inherent to the feedstock (e.g., $K_2CO_3$, $CaCO_3$, and/or $Na_2CO_3$) and/or alkali added for the pretreatment (e.g., NaOH, CaO, MgO, $NH_3$, etc.). For example, without adding alkali and without washing, wheat straw may have an inherent alkali concentration that is between about 0.15 wt % and about 0.63 wt % (OH, on dry solids), whereas bagasse may provide an inherent alkali concentration as high as about 0.2 wt % (OH, on dry solids). Woody feedstock tends to have a much lower inherent alkali concentration (e.g., may be negligible).

In one embodiment, alkali is provided via a recycle or backset stream. For example, in one embodiment, compounds derived from the native lignocellulosic feedstock are introduced into pretreatment via a recycle stream (e.g., leach water may be high in potassium bicarbonate). When calculating the amount of alkali added with these compounds for pretreatment (e.g., less than 0.5 wt % based on dry weight of lignocellulosic biomass), the amount of equivalent OH alkali chemical provided for pretreatment is used.

In one embodiment, alkali is added for the pretreatment in an amount in the range from 0 to 0.5 wt % based on dry weight of incoming lignocellulosic biomass. In one embodiment, organic solvent is added for the pretreatment in an amount in the range from 0 to 5 wt % based on dry weight of incoming lignocellulosic biomass. In one embodiment, carbonyl compound (e.g., aldehyde), or precursor, for forming α-hydroxysulfonic acid is added for the pretreatment in an amount in the range from 0 to 0.5 wt % based on dry weight of incoming lignocellulosic biomass.

The pH (e.g., of the pretreatment liquor and/or the slurry in the pretreatment reactor) may be dependent on the amount of $SO_2$ (and/or other acids) and/or the amount of alkali present. In one embodiment, the pretreatment liquor is prepared by adding alkali to water or to an aqueous solution of $SO_2$ such that the ratio of $SO_2$ to alkali results in excess $SO_2$ (e.g., such that the pH is below about 1.3).

In one embodiment, sufficient $SO_2$ is added to provide an initial pH less than 1.5, less than 1.4, less than 1.3, less than 1.25, less than 1.2, less than 1.15, less than 1.1, less than 1.05, or less than 1.0, measured at ambient temperature. The initial pH reflects the pH near the start of pretreatment after the $SO_2$ has been added to the lignocellulosic biomass (i.e., measured at ambient temperature).

In one embodiment, sufficient $SO_2$ is added to provide a final pH less than 1.25, less than 1.1, less than 1, less than 0.9, or less than 0.8, measured at ambient temperature. The final pH may be measured after the pretreated material is discharged from the pretreatment reactor. In embodiments where the pretreated biomass has a large undissolved solids content and/or is relatively thick, the final pH is measured from a filtrate, pressate, or centrate of the sample (e.g., or other liquid from a solids-liquid separation). In practice, the final pH can be lower than the initial pH.

In one embodiment, the pH (e.g., of pretreatment liquor and/or initial) is achieved by selecting an appropriate ratio of $SO_2$ to alkali. In one embodiment, the ratio of the concentration of $SO_2$ to concentration of alkali, where the concentration of alkali is expressed as weight percent hydroxide, is greater than 30, greater than 35, greater than 40, greater than 45, or greater than 50.

In one embodiment, the alkali concentration is limited to less than about 0.42 wt % (OH, on liquor), while the amount of $SO_2$ provided is sufficient to provide an initial pH less than 1.3. Providing an alkali concentration between 0 and about 0.42 wt % (OH, on liquor), facilitates and/or improves $SO_2$ recovery. Providing an alkali concentration between about 0.1 wt % and about 0.2 wt % (OH, on liquor), can provide an improved enzymatic hydrolysis.

The concentration of $SO_2$ (on liquor, or dry solids) may be determined using titration (e.g., with potassium iodate). However, as this may be challenging when relatively high $SO_2$ concentrations are achieved by introducing $SO_2$ into a pressurizable reactor, the concentration of $SO_2$ may be determined using the $SO_2$ loading. If the reactor has a large headspace (e.g., greater than 75% of the total reactor volume), the concentration of $SO_2$ can take into account the volume of the reactor headspace and partitioning of $SO_2$ into the vapour phase.

The concentration of alkali (on liquor, or dry solids), may be determined using the mass of alkali added to pretreatment and/or the mass of inherent alkali. For example, for lignocellulosic biomass that does not contain significant amounts of inherent alkali (e.g., pine), the concentration of alkali may be determined solely using the amount of alkali added to the pretreatment. For lignocellulosic biomass that contains significant amounts of inherent alkali, the alkali concentration may be determined using the amount of alkali added to the pretreatment, in addition to the amount of alkali inherent to the lignocellulosic biomass. The amount of alkali inherent to the lignocellulosic biomass may be determined by preparing a solution of sulfuric acid ($H_2SO_4$) in water at pH 1.05, 25° C., adding the feedstock to a weight of 5% (dry basis), measuring the resulting pH, and calculating from the acid-base equilibrium of $H_2SO_4$ the weight of OH as a percentage of the weight of feedstock.

In general, the $SO_2$, alkali, bisulfite salt, water, and/or feedstock may be added in any order, or simultaneously, to the pretreatment reactor. For example, the aqueous pretreatment liquor may be prepared prior to being introduced to the pretreatment reactor, within the pretreatment reactor, or a combination thereof. In one embodiment, an aqueous pretreatment liquor containing $SO_2$, alkali, and water is prepared in one or more vessels prior to being introduced into the pretreatment reactor (e.g., which may or may not contain the feedstock).

In one embodiment, an aqueous pretreatment liquor is prepared by adding $SO_2$ to water, to an aqueous solution containing alkali, to an aqueous bisulfite salt solution, or to an aqueous slurry containing the feedstock. In general, the $SO_2$ may be added as a gas, as an aqueous solution, or as a liquid (e.g., under pressure). In one embodiment, the aqueous pretreatment liquor is prepared by adding commercially sourced $SO_2$, by adding $SO_2$ prepared on site (e.g., by burning sulfur), by adding recycled $SO_2$ (e.g., recovered from and/or reused within the process), by adding make-up $SO_2$ (e.g., used to top up the amount of $SO_2$ present), or any combination thereof. Optionally, the aqueous pretreatment liquor is prepared by adding one or more other acids (e.g., $H_2SO_4$, HCl, or lignosulfonic acid (LSA)) in addition to the $SO_2$.

Preparing an aqueous pretreatment liquor containing $SO_2$ and alkali prior to introducing it into the pretreatment reactor may facilitate providing higher $SO_2$ concentrations and/or pre-warming of the pretreatment liquor. In general, the concentration of a $SO_2$ solution may be limited by the solubility of $SO_2$ in water. For example, if no alkali is added, the $SO_2$ concentration may be limited to below about 10 wt % (on liquor) at about 23° C. The $SO_2$ concentration may be increased by cooling the water or aqueous alkali solution prior to bubbling in $SO_2$. Alternatively, or additionally, a higher $SO_2$ concentration may be obtained by introducing the $SO_2$ under pressure. In one embodiment, $SO_2$ is introduced into a vessel to provide an $SO_2$ partial pressure of about 18 psia to about 37 psia, at 25° C. In any case, the pretreatment liquor may or may not be heated prior to entering the pretreatment reactor (e.g., heated under pressure).

In one embodiment, the aqueous pretreatment liquor is prepared using one or more vessels prior to being introduced into the pretreatment reactor. For example, in one embodiment, the aqueous pretreatment liquor is prepared using one or more tanks. In one embodiment, the aqueous pretreatment liquor is prepared using an accumulator, surge tank, and/or buffer tank. Accumulators (or surge tanks), may for example, be used to collect relief gases (e.g., rich in $SO_2$) for direct reuse. Such relief gases may result when it is necessary to vent the pretreatment reactor as the temperature rises.

In one embodiment, the aqueous pretreatment liquor is prepared by feeding $SO_2$ into water or an aqueous solution containing alkali contained in some vessel (e.g., absorption tower). In one embodiment, $SO_2$ is bubbled into a cooled alkali solution. In one embodiment, this $SO_2$/alkali solution is transferred to a pressure accumulator where heat, steam, and/or additional $SO_2$ (e.g., from a relief valve) are added. In one embodiment, the heated pretreatment liquor from the accumulator is introduced into the pretreatment reactor containing the feedstock. In one embodiment, the feedstock is pre-steamed prior to adding the heated pretreatment liquor. In one embodiment, the feedstock is not pre-steamed prior to adding the heated pretreatment liquor. In one embodiment, the preheated pretreatment liquor and feedstock are heated (e.g., to a temperature between about 110° C. and about 160° C.) in the pretreatment reactor.

In one embodiment, a pre-prepared pretreatment liquor (e.g., containing $SO_2$, alkali, and water) and the feedstock are introduced into the pretreatment reactor in a liquor to solid ratio (L/kg) of 9:1, 8:1, 7:1, 6:1, 5:1, 4:1, 3:1, 2:1 or 1.5:1. In one embodiment, the pretreatment is conducted on feedstock having a solids consistency between about 5 wt % and about 51 wt %. In one embodiment, the pretreatment is conducted on a feedstock having a consistency between about 8 wt % and about 35 wt %, between about 12 wt % and about 25 wt %, or between about 10 wt % and 35 wt %.

In one embodiment, the pretreatment is carried out in batch mode, semi-batch mode, or continuous mode, in one or more pretreatment reactors. For example, the pretreatment may be conducted in one or more vertical reactors, horizontal reactors, inclined reactors, or any combination thereof.

In one embodiment, the pretreatment is carried out in batch mode in a steam autoclave. In one embodiment, the pretreatment is conducted in a plug flow reactor. In one embodiment, the pretreatment is conducted in a continuous mode horizontal screw fed reactor. In one embodiment, the pretreatment is conducted in a counter-current flow reactor. In one embodiment, the pretreatment is conducted in reactor provided with a charge of $SO_2$ (e.g., as described in PCT Application No. PCT/CA2016/051089). In one embodiment, the pretreatment is conducted in a digester (e.g., batch or continuous). Such digester may be of any suitable conventional construction (e.g., used in wood pulping).

In one embodiment, the pretreatment is conducted in a pretreatment system, which may include a plurality of components/devices in addition to a pretreatment rector. Some examples of these devices/components include a biomass conveyer, washing system, dewatering system, a plug formation device, a heating chamber, a high shear heating chamber, a pre-steaming chamber, an $SO_2$ impregnation chamber, vapour reservoir chamber, an additional pretreatment reactor, connecting conduits, valves, pumps, etc.

In one embodiment, the pretreatment is conducted in a pretreatment system and/or reactor that is pressurizable. For example, in one embodiment, the pretreatment reactor and/or pretreatment system includes a plurality of valves and/or other pressure increasing, pressure decreasing, or pressure maintaining components for providing and/or maintaining the pretreatment reactor at a specific pressure. Conventional digesters used in wood pulping are generally pressurizable.

In one embodiment, the pretreatment includes adding steam to provide a total pressure between about 190 psia and about 630 psia, between about 200 psia and about 600 psia, between about 250 psia and about 550 psia, or between about 300 psia and about 500 psia. For example, in one embodiment, where the total pressure is about 190 psia, the partial pressure of $SO_2$ may be about 21 psia, whereas the steam partial pressure may be about 169 psia.

In one embodiment, the pretreatment is conducted in a pretreatment system and/or reactor that includes a heater, or some other heating means, for heating the feedstock. Such heating may be direct or indirect (e.g., direct steam heating or indirect steam heating). In one embodiment, the pretreatment reactor and/or the pretreatment system includes direct steam injection inlets (e.g., from a low pressure boiler). For example, in one embodiment, the pretreatment reactor is a digester that provides direct steam injection at the bottom of the digester, with heat transfer throughout the rest of the digester occurring by convection. In one embodiment, the pretreatment reactor is heated by indirect steam heating via the use of one or more heat-exchangers and forced liquor circulation (e.g., using liquid circulation loops). For example, in one embodiment, the aqueous pretreatment liquor is removed from the digester through a screen, and returned to the digester via a pipe, after the circulating liquid is heated with a heat exchanger coupled to the pipe.

In one embodiment, the pretreated material is discharged from the pretreatment reactor under pressure (e.g., blow down). In one embodiment, the discharged pretreated material is collected in a receiving vessel (e.g., a flash tank or blow tank, which may or may not be at atmospheric pressure). In one embodiment, the discharged pretreated material is collected in a diffusion washer. In one embodiment, the discharged pretreated material is fed for downstream processing.

Preparing the Pretreated Material for Enzymatic Hydrolysis

In general, the pretreated material may be subject to one or more steps to prepare it for hydrolysis. For example, in one embodiment the pretreated material is subject to a pressure reduction (e.g., flashing), a liquid/solid separation (e.g., filtering), a washing step, a cooling step, mechanical refining, and/or a pH adjustment step.

In one embodiment, the pretreated biomass is subject to a pressure reduction. For example, in one embodiment, the pressure is reduced using one or more flash tanks in fluid connection with the pretreatment reactor. Flashing may reduce the temperature of the pretreated biomass to 100° C. if an atmospheric flash tank, or lower if a vacuum flash tank.

In one embodiment, the pretreated biomass is subject to a liquid/solid separation, which provides a solid fraction and a liquid fraction. The solid fraction may contain undissolved solids such as unconverted cellulose and/or insoluble lignin. The liquid fraction, which may also be referred to as the xylose-rich fraction, may contain soluble compounds such as sugars (e.g., mannose, xylose, glucose, and arabinose), organic acids (e.g., acetic acid and glucuronic acid), soluble lignin (e.g., including soluble products of reactions between sulfur dioxide/sulfurous acid and lignin, such as lignosulfonic acids), soluble sugar degradation products (e.g., furfural, which may be derived from C5 sugars, and hydroxymethylfurfural (HMF), which may be derived from C6 sugars) and/or one or more salts (e.g., sulfite salts). Exemplary solid/liquid separation methods include, but are not limited to, filtration, membrane filtration, tangential flow filtration (TFF), centrifugation, sedimentation, and flotation. For example, in one embodiment, the pretreated material fed to one or more centrifuges that provide a solid stream and a liquid stream. In one embodiment, the solid/liquid separation uses vacuum or pressure to facilitate the separation. For example, in one embodiment, the pretreated material fed to a filter press or belt press. In one embodiment, the solid/liquid separation is conducted in batch, continuous, or dis-continuous mode.

In one embodiment, the pretreated biomass is subject to one or more washing steps. For example, in one embodiment, the solid fraction from a solid/liquid separation is washed to remove soluble components, including potential inhibitors and/or inactivators. Washing may also remove lignin (e.g., sulfonated lignin). In one embodiment, the pretreated biomass is washed as part of the liquid/solid separation (e.g., as part of decanter/wash cycle). The pretreated biomass may be washed as part of the liquid/solid separation at high or low pressure, which may or may not reduce the temperature of the pretreated biomass. In one embodiment, the wash water is reused or recycled. In one embodiment, the wash water and the liquid fraction are fed to fermentation. In one embodiment, lignin and/or lignosulfonic acid is extracted from the wash water. In one embodiment, the wash water is combined with the liquid fraction and sent for further processing.

In one embodiment, the pretreated biomass is subjected to one or more cooling steps. For example, in one embodiment, the pretreated biomass is cooled to within a temperature range compatible with enzyme(s) added for the enzymatic hydrolysis. For example, conventional cellulases often have an optimum temperature range between about 40° C. and about 60° C., and more commonly between about 50° C. and 55° C., whereas thermostable and/or thermophilic enzymes may have optimum temperatures that are much higher (e.g., as high as, or greater than 80° C.). In one embodiment, the pretreated biomass is cooled to within a temperature range compatible with enzyme(s) and yeast used in a simultaneous saccharification and fermentation (SSF).

In one embodiment, cooling is provided primarily from flashing. In one embodiment, cooling is provided primarily using a heat exchanger. In one embodiment, cooling is provided primarily by washing the solids. In one embodiment, cooling is provided by any combination of flashing, heat exchange, washing, and other cooling techniques. In one embodiment, cooling is provided by injecting a fluid into the pretreated biomass. For example, in one embodiment, cooling is achieved when alkali and/or water is added to the pretreated biomass into order to provide the pH and/or consistency desired for enzymatic hydrolysis.

Advantageously, since the pretreatment is conducted at relatively low temperatures (e.g., between 110° C. and 150° C.), the one or more cooling steps may not have to produce a significant temperature drop.

In one embodiment, the pretreated material is subjected to one or more mechanical refining steps. For example, in one embodiment, the pretreated material (e.g., solid fraction or whole slurry) is subject to a mechanical size reduction using disk refining. Disk refining, may for example, be advantageous when the feedstock includes large woodchips. In one embodiment, disk refining is conducted on the solid fraction after the solid/liquid separation and/or washing.

In one embodiment, the pretreated biomass is subjected to one or more pH adjustment steps. In one embodiment, the pH of the pretreated biomass is adjusted to within a range near the pH optimum of the enzyme(s) used in hydrolysis. For example, cellulases typically have an optimum pH range between about 4 and about 7, more commonly between about 4.5 and about 5.5, and often about 5. In one embodiment, the pH is adjusted to between about 4 and about 8. In one embodiment, the pH is adjusted to between about 4.5 and about 6. In one embodiment, the pH is adjusted so as to substantially neutralize the pretreated biomass.

In one embodiment, the pH of the pretreated biomass is increased as a result of the washing step. In one embodiment, the pH of the pretreated biomass is increased by adding alkali (e.g., calcium hydroxide, potassium hydroxide, sodium hydroxide, ammonia gas, etc.). For example, in one embodiment, sufficient alkali is added to increase the pH of the pretreated biomass to a pH near the optimum pH range of the enzyme(s) used in hydrolysis. In one embodiment, the pH adjustment step includes adding sufficient alkali to overshoot the optimum pH of the enzyme (e.g., overliming), and then adding acid to reduce the pH to near the optimum pH range of the enzyme(s).

In general, the pH adjustment step may be conducted on the solid fraction, the liquid fraction, and/or a combination thereof, and may be conducted before, after, and/or as part of the one or more cooling steps. For example, in embodiments wherein the pretreated biomass is separated into a solid fraction and a liquid fraction, where only the solid fraction is fed to enzymatic hydrolysis, the pH of the liquid fraction may require adjustment prior to being fed to fermentation (e.g., separate from, or with, the hydrolyzate from the solid fraction). For example, in one embodiment, the pH of the liquid fraction is adjusted to the pH optimum of the microorganism used in a subsequent fermentation step. For example, *Saccharomyces cerevisiae* may have optimum pH values between about 4 and about 5.5.

Advantageously, since $SO_2$ pretreatment may use a relatively high amount of free $SO_2$ that is not associated with an added compound (e.g., alkali or carbonyl), flashing of $SO_2$ pretreated biomass may remove a large portion of the $SO_2$, and thus increase the pH of the mixture, so that the pH adjustment step(s) may not have to significantly increase the pH and/or may require less alkali.

In general, the pretreated material prepared for and fed to enzymatic hydrolysis may include the solid fraction, the liquid fraction, or some combination thereof. For example, although the primary goal of enzymatic hydrolysis is to convert the cellulose in the solid fraction to glucose, it may be advantageous to also include the liquid fraction. For example, by feeding the entire pretreated slurry (e.g., cooled and pH adjusted) to enzymatic hydrolysis the solid/liquid separation step can be avoided. Moreover, a washing step can be avoided. While washing may remove potential inhibitors and/or inactivators, and thus may increase enzyme efficiency, it may also remove fermentable sugars, and thus reduce ethanol yield. Providing little or no washing of the pretreated biomass is advantageous in that it requires less process water and provides a simpler process. Nevertheless, some washing may be advantageous in terms of providing a higher glucose yield.

In one embodiment, enzyme is added to and/or mixed with the pretreated biomass (e.g., either the solid fraction or whole) prior to feeding the pretreated biomass to the hydrolysis reactor. In one embodiment, enzyme addition is after cooling and alkali addition.

Enzymatic Hydrolysis

In one embodiment, the pretreated material is fed to one or more enzymatic hydrolysis reactors, wherein cellulose in the solid fraction is converted to glucose. In one embodiment, the pretreated material fed to one or more enzymatic hydrolysis reactors includes washed solids (e.g., washed with water) or whole slurry (e.g., where the liquid and solid fractions are not separated). In one embodiment, the pre-treated material fed to the one or more enzymatic hydrolysis reactors is pH adjusted, detoxified, and/or diluted.

In one embodiment, enzyme is added to and/or mixed with the pretreated material prior to entering the enzymatic hydrolysis reactor and/or within the enzymatic hydrolysis reactor. In one embodiment, enzyme addition is achieved by adding enzyme to a reservoir, such as a tank, to form an enzyme solution, which is then introduced to the pretreated material. In one embodiment, enzyme addition is after cooling and alkali addition. In one embodiment, enzyme addition includes the addition of cellulase.

Cellulases are enzymes that can break cellulose chains into glucose. The term "cellulase", as used herein, includes mixtures or complexes of enzymes that act serially or synergistically to decompose cellulosic material, each of which may be produced by fungi, bacteria, or protozoans. For example, in one embodiment, the cellulase is an enzyme cocktail comprising exo-cellobiohydrolases (CBH), endo-glucanases (EG), and/or β-glucosidases (βG), which can be produced by a number of plants and microorganisms. In one embodiment, the cellulase is a commercial cellulase obtained from fungi of the genera *Aspergillus, Humicola, Chrysosporium, Melanocarpus, Myceliopthora, Sporotrichum* or *Trichoderma*, or from bacteria of the genera *Bacillus* or *Thermobifida*. In addition to CBH, EG and PG, the cellulase may include several accessory enzymes that may aid in the enzymatic digestion of cellulose, including glycoside hydrolase 61 (GH61), swollenin, expansin, lucinen, and cellulose-induced protein (Cip). In one embodiment, the enzyme includes a lytic polysaccharide monooxygenase (LPMO) enzyme. For example, in one embodiment, the enzyme includes GH61. In one embodiment, the cellulase is a commercial cellulase composition that is suitable for use in the methods/processes described herein. In one embodiment, one or more cofactors are added. In one embodiment, $O_2$ or $H_2O_2$ is added. In one embodiment, ascorbic acid or some other reducing agent is added. In one embodiment, the pH is adjusted during the enzymatic hydrolysis.

In general, the enzyme dose may depend on the activity of the enzyme at the selected pH and temperature, the reaction time, the volume of the reactor, and/or other parameters. It should be appreciated that these parameters may be adjusted as desired by one of skill in the art.

In one embodiment, cellulase is added at a dosage between about 2 to 20 mg protein per gram cellulase. In one embodiment, the cellulase is added at a dosage between about 2 to 15 mg protein per gram cellulase. In one embodiment, the cellulase is added at a dosage between about 2 to 12 mg protein per gram cellulase. The protein may be quantified using either the bicinchoninic acid (BCA) assay or the Bradford assay. In one embodiment, the initial concentration of cellulose in the slurry, prior to the start of enzymatic hydrolysis, is between about 0.01% (w/w) to about 20% (w/w).

In one embodiment, the enzymatic hydrolysis is carried out at a pH and temperature that is at or near the optimum for the added enzyme. For example, in one embodiment, the enzymatic hydrolysis is carried out at one or more temperatures between about 30° C. to about 95° C. In one embodiment, the enzymatic hydrolysis is carried out at one or more temperatures between about 50° C. and about 60° C. In one embodiment, the enzymatic hydrolysis is carried out at one or more temperatures between about 45° C. and about 55° C. In one embodiment, the enzymatic hydrolysis is carried such that the initial pH is, and/or such that the pH is maintained, between about 3.5 and about 8.0. In one embodiment, the enzymatic hydrolysis is carried such that the initial pH is, and/or such that the pH is maintained, between about 4 and about 6. In one embodiment, the enzymatic hydrolysis is carried such that the initial pH is, and/or such that the pH is maintained, between about 4.8 and about 5.5.

In one embodiment, the enzymatic hydrolysis is carried out for a time period of about 10 to about 250 hours. In one embodiment, the enzymatic hydrolysis is carried out for a time period of about 50 to about 250 hours. In one embodiment, the enzymatic hydrolysis is carried out for at least 24 hours. In one embodiment, the enzymatic hydrolysis is carried out for at least 36 hours. In one embodiment, the enzymatic hydrolysis is carried out for at least 48 hours. In one embodiment, the enzymatic hydrolysis is carried out for at least 72 hours. In one embodiment, the enzymatic hydrolysis is carried out for at least 80 hours. In general, conducting the enzymatic hydrolysis for at least 24 hours will promote hydrolysis of both the amorphous and crystalline cellulose.

In one embodiment, the enzymatic hydrolysis includes agitation. Agitation may improve mass and/or heat transfer and may provide a more homogeneous enzyme distribution. In addition, agitation may entrain air in the slurry, which may be advantageous when the enzyme contains a LPMO. In one embodiment, air and/or oxygen is added to the hydrolysis. In one embodiment, air and/or oxygen is added to the hydrolysis using a pump or compressor in order to maintain the dissolved oxygen concentration within a range that is sufficient for the full activity of LPMOs or any other oxygen-dependent components of the catalyst used to effect hydrolysis. In one embodiment, air or oxygen is bubbled into the slurry or headspace of one or more of the hydrolysis reactors.

In one embodiment, the enzymatic hydrolysis is conducted as a batch process, a continuous process, or a combination thereof. In one embodiment, the enzymatic hydrolysis is agitated, unmixed, or a combination thereof. In one embodiment, the enzymatic hydrolysis is conducted in one or more dedicated hydrolysis reactors, connected in series or parallel. In one embodiment, the one or more hydrolysis reactors are jacketed with steam, hot water, or other heat sources.

In one embodiment, the enzymatic hydrolysis is conducted in one or more continuous stirred tank reactors (CSTRs) and/or one or more plug flow reactors (PFRs). In plug flow reactors, the slurry is pumped through a pipe or tube such that it exhibits a relatively uniform velocity profile across the diameter of the pipe/tube and such that residence time within the reactor provides the desired conversion. In one embodiment, the hydrolysis includes a plurality of hydrolysis reactors including a PFR and a CSTR in series.

In one embodiment, the enzymatic hydrolysis and fermentation are conducted in separate vessels so that each biological reaction can occur at its respective optimal temperature. In one embodiment, the enzymatic hydrolysis and fermentation are conducted in the same vessel, or series of vessels.

In one embodiment, the hydrolyzate provided by enzymatic hydrolysis is filtered to remove insoluble lignin and/or undigested cellulose.

Fermentation

In one embodiment, the sugars produced during enzymatic hydrolysis and/or pretreatment are fermented via one or more microorganisms to produce a fermentation product (e.g., an alcohol such as ethanol or butanol). In general, the fermentation microorganism(s) may include any suitable yeast and/or bacteria.

In one embodiment, the hydrolyzate produced during enzymatic hydrolysis is subjected to a fermentation with *Saccharomyces* spp. yeast. For example, in one embodiment, the fermentation is carried out with *Saccharomyces cerevisiae*, which has the ability to utilize a wide range of hexoses such as glucose, fructose, sucrose, galactose, maltose, and maltotriose to produce a high yield of ethanol. In one embodiment, the glucose and/or other hexoses derived from the cellulose are fermented to ethanol using a wild-type *Saccharomyces cerevisiae* or a genetically modified yeast. In one embodiment, the fermentation is carried out with *Zymomonas mobilis* bacteria.

In one embodiment, the hydrolyzate produced during enzymatic hydrolysis is fermented by one or more microorganisms to produce a fermentation broth containing butanol. For example, in one embodiment the glucose produced during enzymatic hydrolysis is fermented to butanol with *Clostridium acetobutylicum*.

In one embodiment, one or more of the pentoses produced during the pretreatment is fermented to ethanol via one or more organisms. For example, in one embodiment, the xylose and/or arabinose produced during the pretreatment is fermented to ethanol with a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis*.

In one embodiment, the xylose and other pentose sugars produced during the pretreatment are fermented to xylitol by yeast strains selected from the group consisting of *Candida, Pichia, Pachysolen, Hansenula, Debaryomyces, Kluyveromyces* and *Saccharomyces*.

In general, the C6 sugar from the enzymatic hydrolysis and the C5 sugars from the liquid fraction of the pretreated biomass can be subjected to separate fermentations or a combined fermentation. For example, consider the case where the pretreated biomass is subject to a solid/liquid separation and only the solid fraction is fed to enzymatic hydrolysis. In this case, the glucose produced by enzymatic hydrolysis can be fermented on its own, or can be combined with the liquid fraction and then fermented. For example, in one embodiment, a sugar solution containing both the C5 and C6 sugars is fermented to ethanol using only *Saccharomyces cerevisiae*. In one embodiment, a sugar solution containing both C5 and C6 sugars is fermented to ethanol using a mixture wherein C5 utilizing and ethanol producing yeasts (e.g., such as *Pichia fermentans* and *Pichia stipitis*) are cocultured with *Saccharomyces cerevisiae*. In one embodiment, a sugar solution containing both C5 and C6 sugars is fermented using genetically engineered *Saccharomyces* yeast capable of cofermenting glucose and xylose.

In general, the dose of the microorganism(s) will depend on a number of factors, including the activity of the microorganism, the desired reaction time, the volume of the reactor, and/or other parameters. It should be appreciated that these parameters may be adjusted as desired by one of skill in the art to achieve optimal conditions. In one embodiment, the fermentation is supplemented with additional nutrients required for the growth of the fermentation microorganism. For example, yeast extract, specific amino acids, phosphate, nitrogen sources, salts, trace elements and vitamins may be added to the hydrolyzate slurry to support their growth. In one embodiment, yeast recycle is employed.

In one embodiment, the fermentation is carried out at a pH and temperature that is at or near the optimum for the added microorganism. For example, *Saccharomyces cerevisiae* may have optimum pH values between about 4 and about 5.5 and a temperature optimum between about 25° C. and about 35° C. In one embodiment, the fermentation is carried out at one or more temperatures between about 25° C. to about 55° C. In one embodiment, the fermentation is carried out at one or more temperatures between about 30° C. to about 35° C.

In general, the fermentation may be conducted as a batch process, a continuous process, or a fed-batch mode. For example, in one embodiment, the fermentation is conducted in continuous mode, which may offer greater productivity and lower costs. In one embodiment, the enzymatic hydrolysis may be conducted in one or more fermentation tanks, which can be connected in series or parallel. In general, the fermentation may be agitated, unmixed, or a combination thereof. For example, in one embodiment, the fermentation is conducted one or more continuous stirred tank reactors (CSTRs) and/or one or more plug flow reactors (PFRs). In one embodiment, the one or more fermentation tanks are jacketed with steam, hot water, or other heat sources.

In one embodiment, the enzymatic hydrolysis and fermentation are conducted in separate vessels so that each biological reaction can occur at its respective optimal temperature. In another embodiment, the hydrolysis (e.g., which may be also referred to as saccharification) is conducted simultaneously with the fermentation in same vessel. For example, in one embodiment, a simultaneous saccharification and fermentation (SSF) is conducted at temperature between about 35° C. and 38° C., which is a compromise between the 50° C. to 55° C. optimum for cellulase and the 25° C. to 35° C. optimum for yeast.

Fermentation Product Recovery

In one embodiment, the fermentation product is recovered. For example, in one embodiment, the fermentation product is an alcohol and is subject to an alcohol recovery process wherein the alcohol is concentrated and/or purified from the fermented solution. In one embodiment, the fermentation broth is subject to a solid/liquid separation (e.g., filtered) and the liquid fraction is fed to a distillation system. In one embodiment, the fermentation broth, which may include unconverted cellulose, insoluble lignin, and/or other undissolved substances, is fed to the distillation system without being pre-filtered.

In one embodiment, the fermentation produces ethanol, which is recovered using one or more distillation columns that separate the ethanol from other components (e.g., water). In general, the distillation column(s) in the distillation unit may be operated in continuous or batch mode, although are typically operated in a continuous mode. Heat for the distillation process may be introduced at one or more points, either by direct steam injection or indirectly via heat exchangers. After distillation, the water remaining in the concentrated ethanol stream (i.e., vapour) may be removed from the ethanol rich vapour by molecular sieve resin, by membrane extraction, or other methods known to those of skill in the art for concentration of ethanol beyond the 95% that is typically achieved by distillation (e.g., a vapour phase drying). The vapour may then be condensed and denatured.

Sulfur Dioxide Recovery

Excess $SO_2$ not consumed during the pretreatment can be recovered and/or recycled. For example, in one embodiment, $SO_2$ not consumed during the pretreatment is forced out of the pretreated slurry by a pressure reduction (e.g., top relief, atmospheric flash, vacuum flash, vacuum, etc.) or by a temperature increase (e.g., evaporation by heating). The $SO_2$ forced out of the pretreated slurry can be collected, recovered, and/or recycled within the process. In one embodiment, the $SO_2$ forced out of the pretreated slurry is fed to an $SO_2$ recovery unit. For example, in one embodiment, the slurry of pretreated material is flashed, and the flash stream, which contains the excess $SO_2$, is fed to a $SO_2$ recovery unit. In one embodiment, the $SO_2$ forced out of the pretreated slurry is reused directly (e.g., fed to an accumulator or the pretreatment reactor).

In general, the $SO_2$ recovery unit may be based on any suitable $SO_2$ recovery technology, as known in the art. In one embodiment, the $SO_2$ recovery unit includes a partial condenser, an $SO_2$ stripper, and/or an $SO_2$ scrubbing system. In one embodiment, the $SO_2$ recovery unit includes a $SO_2$ scrubbing system, which may include one or more packed absorbers (e.g., amine-based, alkali-based, or other absorbers). In one embodiment, the $SO_2$ recovery unit provides purified $SO_2$ that can be recycled for use in the pretreatment. In one embodiment, the $SO_2$ recovery unit provides partially purified $SO_2$ that can be recycled for use in the pretreatment.

In one embodiment, the recovered $SO_2$, which is optionally stored temporarily, is recycled directly back into the process. Advantageously, $SO_2$ recovery allows the recycling of sulfur within the system, and thus improves the process economics (e.g., since less $SO_2$ needs to be acquired for pretreatment).

Providing relatively high $SO_2$ loadings without a volatile solvent (e.g., ethanol) and providing limited or no added alkali may advantageously facilitate a simple flash steam recovery of sulfur dioxide. In addition, it simplifies any further purification and/or processing of the $SO_2$ recovered from the flash stream. Since the recovery may be relatively simple and efficient, the cost of the relatively high sulfur loading is not as limiting. Accordingly, the advantages of using a high sulfur loading for low temperature pretreatment may be exploited.

Advantageously, using a relatively high sulfur loading (e.g., greater than 20 wt %, or greater than 25 wt %, based on dry weight of lignocellulosic biomass) and $SO_2$ recovery from the flash, when at least 30% to 100% of the $SO_2$ in the flash is recovered and/or recycled improves the economics of the process.

Additional Product Recovery

Although a key goal of the process is to convert cellulose to glucose, which may then be converted to a fermentation product (e.g., ethanol), one or more other products may be produced during the process. Producing one or more additional products, and/or improving the yield of glucose/fermentation product, from the non-cellulose components (e.g., from hemicellulose and/or lignin) may be advantageous.

Depending on the pretreatment conditions, in addition to unconverted cellulose, the pretreated slurry may contain hemicellulose sugars (e.g., mannose, xylose, glucose), organic acids (e.g., acetic acid), soluble lignin (e.g., lignosulfonate), soluble sugar degradation products (e.g., furfural and HMF), and/or one or more salts (e.g., sulfite salts).

In one embodiment, one or more products derived from the hemicellulose sugars are produced and/or recovered. For example, in one embodiment, wherein the pretreated slurry is subject to a solid/liquid separation and the solids are fed to enzymatic hydrolysis, the liquid fraction may be subject to separate processing.

In one embodiment, the liquid fraction is pH adjusted, detoxified, and/or cooled prior to being fed to a fermenter. In this embodiment, the hemicellulose sugars may be fermented separately from the glucose produced during enzymatic hydrolysis or may be fermented with the glucose produced during enzymatic hydrolysis. Advantageously, this embodiment may improve the fermentation product (e.g., ethanol) yield.

In one embodiment, the liquid fraction is fed to an anaerobic digester, wherein the organic contents may be converted to biogas. In one embodiment, the liquid fraction is fed to a wet oxidation, wherein the organic contents may be converted to acetic acid or acetate. In one embodiment, the biogas and/or acetic acid is used as a feedstock to produce ethanol via a gas fermentation that uses carbon monoxide, carbon dioxide, and/or hydrogen as a substrate. Advantageously, this improves the ethanol yield as ethanol is produced from the cellulose component as well as from the hemicellulose and/or lignin components. In one embodiment, the biogas is used within the process in order to reduce greenhouse gas emissions. In one embodiment, the biogas is upgraded to pipeline standards and provided or allocated for transportation use or for use in producing a transportation fuel. This embodiment is particularly advantageous because in using a pretreatment liquor having a pH below about 1.3 and a relatively high $SO_2$ concentration, both the hemicellulose and lignin dissolution are improved, which may improve the product yield from these fractions.

In one embodiment, lignosulfonate generated during the pretreatment is recovered. The term lignosulfonate refers to water soluble sulfonated lignin (i.e., soluble in water at neutral and/or acid conditions) and encompasses both lignosulfonic acid and its neutral salts. In general, lignosulfonate may be recovered following pretreatment, enzymatic hydrolysis, and/or fermentation. In one embodiment, lignosulfonate is recovered for energy production (e.g., combusted). In one embodiment, lignosulfonate is recovered for producing value-added materials (e.g., a dispersing agent, a binding agent, a surfactant, an additive in oil and gas drilling, an emulsion stabilizer, an extrusion aid, to produce vanillin, for dust control applications, etc.).

In general, lignosulfonate may be recovered by any method used to produce lignosulfonate products (e.g., provided in liquid form or as a powder). For example, lignosulfonate may be recovered using a method conventionally used for recovering lignosulfonates from waste liquor (e.g., brown or red) of a sulfite pulping process. In one embodiment, lignosulfonate is recovered by precipitation and subsequent filtering, membrane separation, amine extraction, ion exchange, dialysis, or any combination thereof.

To facilitate a better understanding of embodiments of the instant invention, the following examples of certain aspects of some embodiments are given. In no way should the following examples be read to limit, or define, the entire scope of the invention.

EXAMPLES

Example 1: Low Temperature $SO_2$ Pretreatment of Wheat Straw

Low temperature $SO_2$ pretreatment of wheat straw was conducted in pressure tube reactors (PT), which are 110 mL glass tubes (e.g., about 7 inches in length). The wheat straw was hammer-milled such that a large portion of the particles was less than about 1 inch (2.54 cm) length and ¼ inch (0.635 cm) width. In general, less than 5% of the particles were longer than 2 inches (5.08 cm) and up to 10% of the particles were fines, the size of dust.

The glucan content of the straw was 34.61%, the xylan content was 20.09%, and the lignin content was 20.49% on a dry basis. The total solids (TS) content of the straw was 93.25%, which equates to 6.75% moisture. The carbohydrate assay was based on Determination of Structural Carbohydrates and Lignin in Biomass-LAP (Technical Report NREL/TP-510-42618).

Solutions of 6%, 4%, and 2% $H_2SO_3$ (w/w) were freshly prepared in 500 mL bottles from sulfurous acid solution (≥6% $H_2SO_3$, from Sigma-Aldrich). The sulfurous acid solutions were added to the wheat straw in the reactors and the reactors were sealed immediately. Each reactor was cooked at the pretreatment temperature of 130° C., in a preheated steam autoclave, for the selected pretreatment time. The pretreatment time does not include the time for the autoclave to reach the pretreatment temperature (e.g., about 20 minutes). At the end of the pretreatment, the reactors were cooled in an ice bath. The contents of the pressure tubes (e.g., pretreated material) was removed, weighed, and combined in a sealable plastic bag. A portion of the pretreated material was removed for washing, to prepare a washed pretreatment sample.

All experiments conducted with or based on $SO_2$/sulfurous acid were carried out in a fume hood, including the drying of samples for determining the dissolved solids and total solids concentrations.

The total amount of $SO_2$ available for pretreatment, as calculated for various $SO_2$ pretreatments is shown below. In each case, the consistency of the slurry to be pretreated was about 10 wt %.

TABLE 1

Pretreatment conditions for various low temperature $SO_2$ pretreatments

| Exp | Mass of dry biomass (g) | Concentration of $H_2SO_3$ (w/w %) (about 52 mL) | Total amount of $SO_2$ (wt % based on dry weight of lignocellulosic biomass) | Initial pH | Pretreatment temperature (° C.) | Pretreatment time (min) |
|---|---|---|---|---|---|---|
| 1 | 6 | 2 | 14 | 1.47 | 130 | 180 |
| 2 | 6 | 4 | 28 | 1.26 | 130 | 180 |
| 3 | 6 | 6 | 42 | 1.13 | 130 | 180 |

In general, the pretreated wheat straw produced from the low temperature $SO_2$ pretreatments at 14, 28, and 42 wt % $SO_2$ (based on dry weight of lignocellulosic biomass) was found to visually resemble the non-treated material, albeit slightly darker. Even when the total amount of $SO_2$ was above 74 wt % (based on dry weight of lignocellulosic biomass), for a 60 minute cook at 130° C., the pretreated wheat straw, although somewhat broken down, resembled raw fiber, but darker. Notably, the low temperature $SO_2$ pretreatment produced a pretreated material that is easy to wash and/or filter.

For comparative purposes, low temperature $H_2SO_4$ pretreatment of wheat straw was also conducted in pressure tube reactors (PT). The slurry, having an initial consistency of about 10 wt %, was prepared using 0.5 (w/w) % $H_2SO_4$, so that the total amount of $H_2SO_4$ was about 4.5 wt % based on dry weight of lignocellulosic biomass, the pretreatment temperature was 130° C., and the pretreatment time was 180 minutes. The pretreatment conditions for this low temperature $H_2SO_4$ pretreatment are shown in Table 2. Notably, the initial pH for the 4.5 wt % $H_2SO_4$ low temperature pretreatment and the 14 wt % $SO_2$ low temperature pretreatment were both 1.47.

TABLE 2

Pretreatment conditions for a low temperature $H_2SO_4$ pretreatment

| Mass of dry biomass (g) | Concentration of $H_2SO_4$ (w/w %) (about 52 mL) | Amount of $H_2SO_4$ (wt % based on dry weight of lignocellulosic biomass) | Initial pH | Pretreatment temperature (° C.) | Pretreatment time (min) |
|---|---|---|---|---|---|
| 6 | 0.5 | 4.5 | 1.47 | 130 | 180 |

The low temperature $SO_2$ pretreatment was also compared to a high temperature $SO_2$ pretreatment of wheat straw, conducted in a stainless steel tubular reactor. The pretreatment conditions are shown in Table 3, where the initial consistency was about 10%.

TABLE 3

Pretreatment conditions for a high temperature $SO_2$ pretreatment

| Mass of dry biomass (g) | Concentration of $H_2SO_3$ (w/w %) (about 13.5 mL) | Total amount of $SO_2$ (wt % based on dry weight of lignocellulosic biomass) | Initial pH | Pretreatment temperature (° C.) | Pretreatment time (min) |
|---|---|---|---|---|---|
| 1.5 | 3 | 21 | 1.4 | 230 | 3.7 |

The low temperature $SO_2$ pretreatment is also compared to a high temperature $H_2SO_4$ pretreatment of wheat straw, conducted in a steam gun. The pretreatment conditions are shown in Table 4. In this case, wheat straw was soaked overnight in a solution of $H_2SO_4$ having a pH of 1.4, and was pretreated at a consistency of 30%.

TABLE 4

Pretreatment conditions for a high temperature $H_2SO_4$ pretreatment

| Mass of dry biomass (g) | Concentration of $H_2SO_4$ (w/w %) | Amount of $H_2SO_4$ (wt % based on dry weight lignocellulosic biomass) | Initial pH | Pretreatment temperature (° C.) | Pretreatment time (min) |
|---|---|---|---|---|---|
| 240 | 0.54 | 1.26 | 1.4 | 200 | 2 |

A portion of the $SO_2$ pretreated material was reserved for analysis. Undissolved solids (UDS) concentration, total solids (TS) concentration, dissolved solids (DS) concentration, can be determined using methods accepted in the art. For example, UDS, TS, and DS are calculated according the methodology set out in Examples 3, 4, and 5 of U.S. Pat. No. 9,574,212.

The concentration of monomeric sugars (e.g., concentration of glucose and/or xylose) in the pretreated material can be determined using high performance liquid chromatography (HPLC). For example, the concentration of monomeric sugars such as xylose is calculated according the methodology set out in Example 6 of U.S. Pat. No. 9,574,212.

The filtrate from a portion of the pretreated material produced using the pretreatment conditions in the last row of Table 1 (Experiment 3), was found to contain 2.04 g/L glucose, 22.7 g/L xylose, and 0.04 g/L of furfural.

The carbohydrate content of the $SO_2$ pretreated material can be ascertained with a carbohydrate assay based on Determination of Structural Carbohydrates and Lignin in Biomass-LAP (Technical Report NREL/TP-510-42618). This assay can provide the cellulose content, xylan content, insoluble lignin content, and lignin content of the pretreated biomass, w/w on a dry basis. For example, the cellulose/glucan content, xylan content, and/or lignin content is determined using the methodology set out in Example 11 of U.S. Pat. No. 9,574,212.

Figure 2:
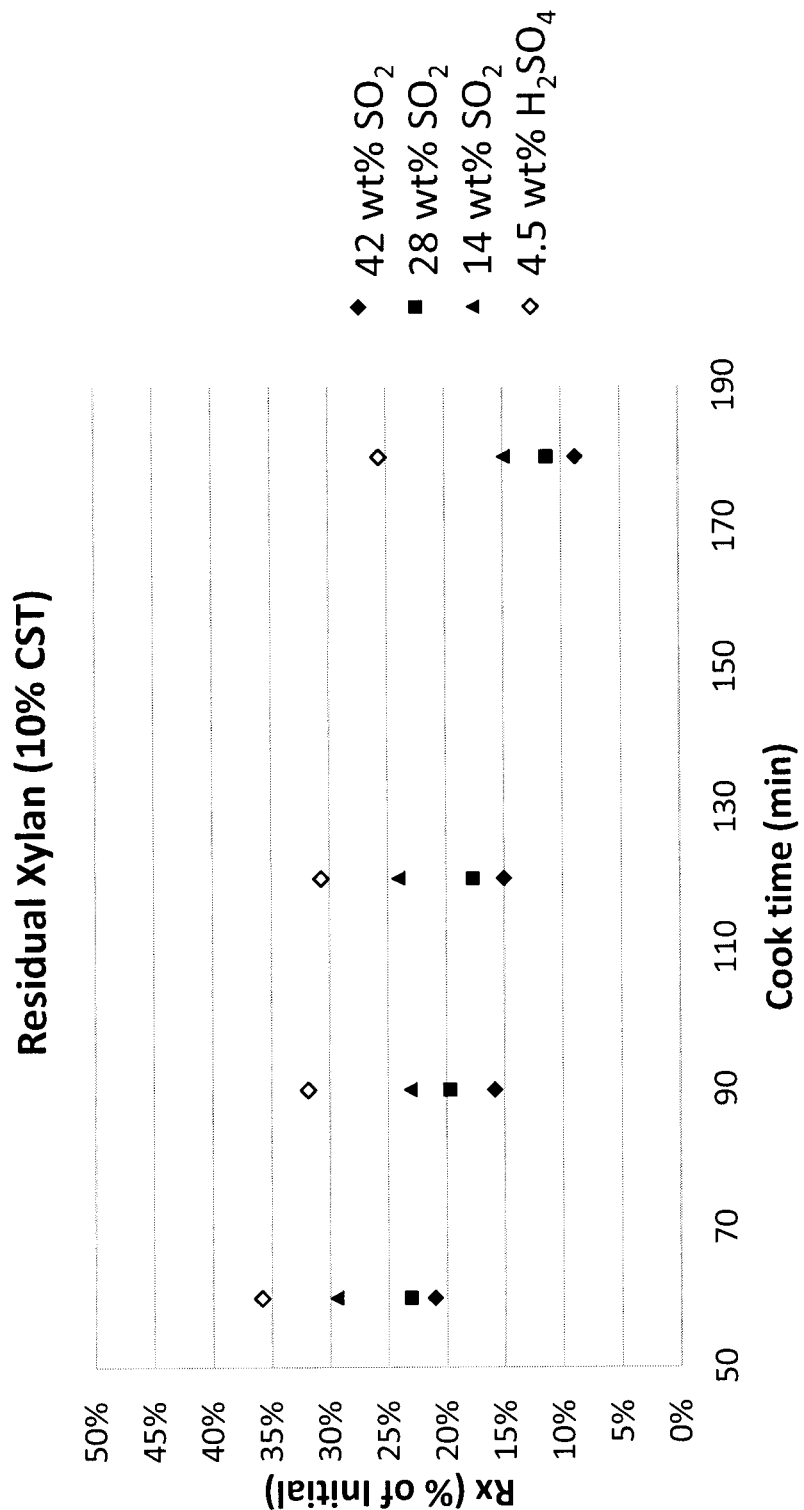
FIG. 2 is plot showing residual xylan ($R_x$) as a function of pretreatment time for $SO_2$ pretreatment of wheat straw at 130° C.

The residual xylan ($R_x$) and lignin dissolution provided by the pretreatment is calculated relative to the untreated lignocellulosic biomass. The residual xylan for low temperature $SO_2$ pretreated wheat straw, where the pretreatment temperature was 130° C. and the consistency of the initial wheat straw slurry was 10 wt %, is shown in FIG. 2. Lignin dissolution for low temperature $SO_2$ pretreated wheat straw, where the pretreatment temperature was 130° C. and the consistency of the initial wheat straw slurry was 10 wt %, is shown in FIG. 3.

Referring to FIG. 2, residual xylan ($R_x$) was found to be as low as about 10 wt % when the total amount of $SO_2$ is 28 or 42 wt %, based on dry weight of lignocellulosic biomass, and the cooking time is at least 180 minutes. Increasing severity by extending the pretreatment time to 360 minutes (not shown) reduces the residual xylan to less than 5%. Advantageously, the concentration of xylose produced during the pretreatment has been found to be relatively stable up to about 3.5 hours of pretreatment (e.g., with over 80%) recovery. Notably, the low temperature $SO_2$ pretreatment where the total amount of $SO_2$ is 14 wt % dry lignocellulosic biomass resulted in lower residual xylan than the low temperature $H_2SO_4$ pretreatment where the amount of $H_2SO_4$ is 4.5 wt % based on dry weight of lignocellulosic biomass.

Figure 3:
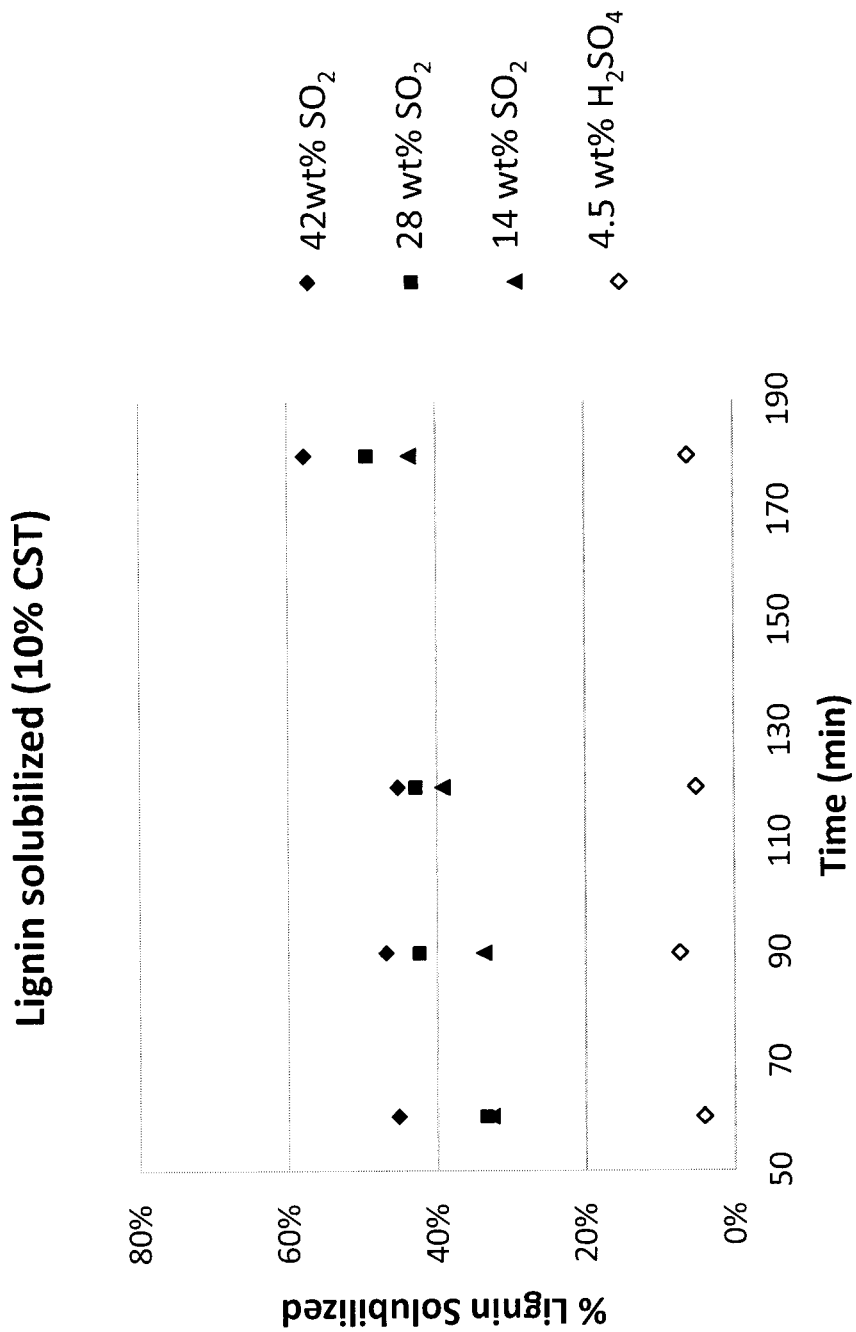
FIG. 3 is plot showing lignin dissolution as a function of pretreatment time for $SO_2$ pretreatment of wheat straw at 130° C.

Referring to FIG. 3, lignin dissolution is very good for the low temperature $SO_2$ pretreatment, but not good for the low temperature $H_2SO_4$ pretreatment. Remarkably, lignin dissolution reached or exceeded about 50% at the higher pretreatment times and $SO_2$ concentrations, without having to use added alkali and/or organic solvent.

Example 2: Enzymatic Hydrolysis of $SO_2$ Pretreated Wheat Straw

Washed pretreatment samples were prepared by suspending a portion of pretreated sample in ultra-purified water (Milli-Q™), filtering the suspension through glass fiber filter paper (G6, 1.6 microns), and then repeating the alternating steps. The washed pretreatment solids were hydrolyzed in 50 mL Erlenmeyer flasks, at a consistency of about 10 wt %, with sodium citrate (1 M of citrate buffer pH added to a final concentration of 0.1M). The flasks were incubated at 52° C., with moderate shaking at about 250 rpm, for 30 minutes to equilibrate substrate temperature.

Hydrolysis was initiated by adding liquid cellulase enzyme. Enzyme was added at a dosage of 5 mg/g (i.e., mg protein/g of cellulose). The flasks were incubated at 52° C. in an orbital shaker (250 rpm) for various hydrolysis times (e.g., 200 hours). The hydrolysis was followed by measuring the sugar monomers in the hydrolysate. More specifically, aliquots obtained at various hours of hydrolysis, were used to analyze the sugar content. Each aliquot was obtained at the specific time interval by swirling the flask, withdrawing 700 μL of the flask contents with a wide-bore pipette tip and depositing it in a 1.5 mL Eppendorf centrifuge tube, placing the centrifuge tube in a heating block for 10 minutes to deactivate the enzyme, and storing the aliquot at about 4° C. for subsequent sugar analysis.

To assay samples for monomeric sugars, the samples were warmed to room temperature and were centrifuged for 4 minutes at 14,800 rpm. The supernatant was diluted in water for measuring the glucose with HPLC. The HPLC measured amount of glucose was used to determine the cellulose conversion. The cellulose conversion, which is expressed as the amount of glucose released during enzymatic hydrolysis of the solid fraction, and thus may also be referred to as glucose conversion, was determined using the following equation and the methodology outlined in Example 9 of U.S. Pat. No. 9,574,212.

Cellulose conversion=concentration of glucose in aliquot/maximum glucose at 100% conversion.

Figure 4:
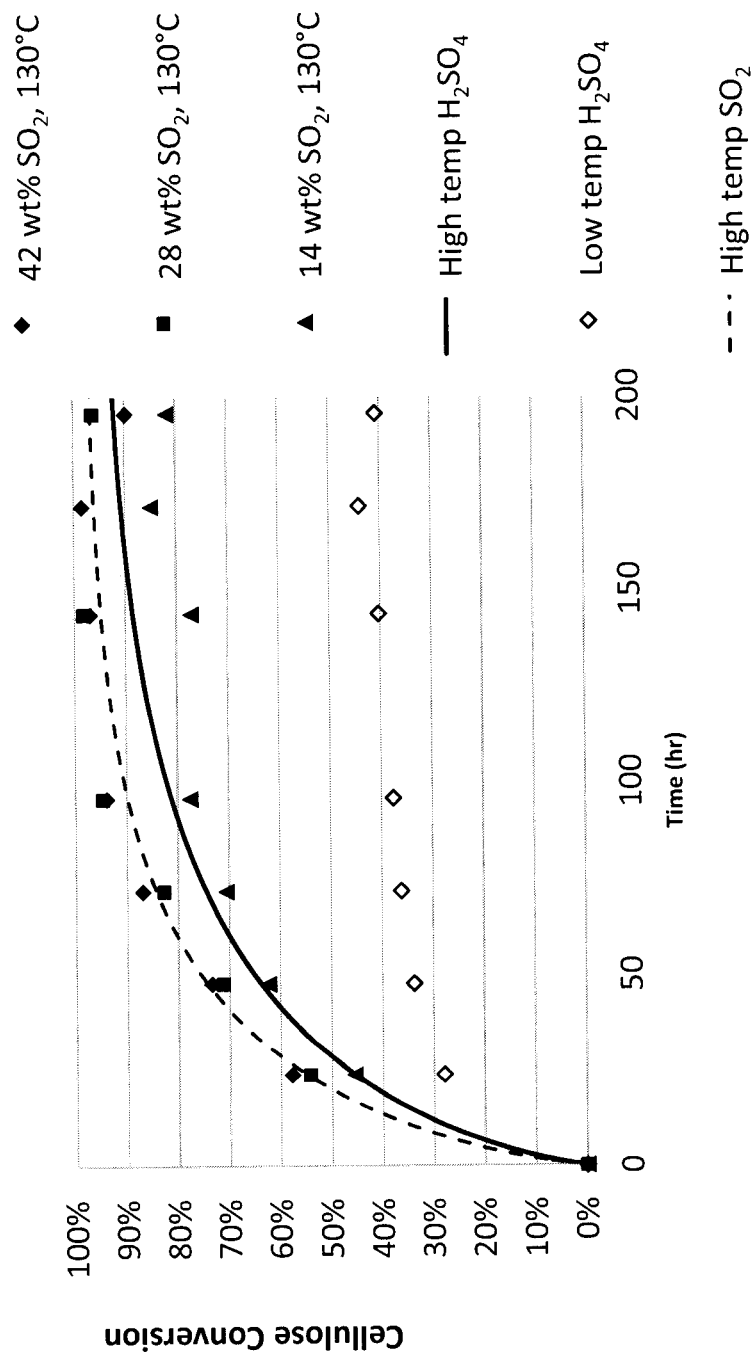
FIG. 4 is a plot of cellulose conversion versus hydrolysis time for the enzymatic hydrolysis of wheat straw subjected to a $SO_2$ pretreatment at 130° C. 180 minutes, for different total $SO_2$ amounts, shown relative to the cellulose conversion of wheat straw subjected to a low temperature $H_2SO_4$ pretreatment (i.e., at 130° C. for 180 minutes), high temperature $H_2SO_4$ pretreatment (i.e., at 200° C. for 2 minutes), and high temperature $SO_2$ pretreatment (i.e., at 230° C. for 3.7 minutes)

FIG. 4 shows a plot of cellulose conversion for the enzymatic hydrolysis of washed solids of a $SO_2$ pretreatment conducted at 130° C. and 10% consistency, for 180 minutes, where the total amount of $SO_2$ is 42 wt %, 28 wt %, or 14 wt %, based on dry weight of lignocellulosic biomass. For reference, these results are illustrated next to the glucose conversion for the enzymatic hydrolysis of washed solids from the low temperature $H_2SO_4$ pretreatment (i.e., at 130° C. for 180 minutes), the high temperature $H_2SO_4$ pretreatment (i.e., 200° C. for 2 minutes), and the high temperature $SO_2$ pretreatment (i.e., 230° C. for 3.7 minutes). The latter two glucose conversion plots correspond to data fit by non-linear regression and correspond to pretreatment conditions that were previously optimized.

Surprisingly, the low temperature $SO_2$ pretreatment was able to produce a glucose conversion greater than that achieved by the high temperature $H_2SO_4$ pretreatment, and similar to that provided the high temperature $SO_2$ pretreatment (e.g., when the total amount of $SO_2$ is at least 28 wt % based on dry weight of lignocellulosic biomass). Remarkably, these improvements are provided without having to add solvent, alkali, or carbonyl compounds. Accordingly, both capital and operating costs may be lower, and $SO_2$ recovery may be simplified.

Moreover, since xylose is relatively stable at these low temperature pretreatment conditions, the xylose yield may be larger and/or the concentration of potential inhibitors may be relatively low. For example, wheat straw pretreated at 130° C. with a total amount of $SO_2$ equal to about 42 wt % based on dry weight of lignocellulosic biomass (e.g., see Table 1) was found to contain <0.1 g/L of furfural, whereas wheat straw pretreated at 230° C. with a total amount of $SO_2$ equal to about 21 wt % based on dry weight of lignocellulosic biomass (e.g., see Table 3) was found to contain about 0.9 g/L of furfural.

Notably, the low temperature $SO_2$ pretreatments are much more efficient than the low temperature $H_2SO_4$ pretreatment. For example, although the low temperature pretreatments using 4.5 wt % $H_2SO_4$ and 14 wt % $SO_2$, based on dry weight of lignocellulosic biomass, both had a similar initial pH, the low temperature $SO_2$ pretreatment had a glucose yield that was approximately doubled after 96 hours of hydrolysis, relative to the low temperature $H_2SO_4$ pretreatment. Moreover, for wheat straw, the low temperature $SO_2$ pretreatment has been found to require about ¼ of the enzyme to produce the same cellulose conversion as the low temperature $H_2SO_4$ pretreatment.

Example 3: Low Temperature Pretreatment of Bagasse with $SO_2$

Pretreatment of bagasse with $SO_2$ was conducted in 25 mL, stainless steel, laboratory tubular reactors (i.e., about 5 inches in length). The bagasse, which was hammer-milled, had a a cellulose/glucan content of 40.13%, xylan content of 22.26%, a lignin content of 25.40%, and a total solids (TS) content of 91.66%, w/w on a dry basis. The carbohydrate assay was based on Determination of Structural Carbohydrates and Lignin in Biomass-LAP (Technical Report NREL/TP-510-42618).

Stock sulfurous acid solution having a $SO_2$ concentration between about 10.9 wt % and about 12.5 wt % (on liquor) (e.g., about 14 wt % to 16 wt % $H_2SO_3$ on liquor) was prepared by bubbling $SO_2$ into Milli-Q water cooling in an ice bath. The exact concentration of the sulfurous acid stock solution was determined using back titration with HCl (0.1M). The sulfurous acid stock solution was stored at about 4° C. Stock $NaHSO_3$ solutions were prepared by adding $NaHSO_3$ to degassed Milli-Q water and stored in filled sealed vials to eliminate headspace.

Pretreatment slurries were prepared by adding bagasse to each laboratory tubular reactor, followed by a quantity of water calculated to provide the target $SO_2$ and alkali concentrations (e.g., based on the concentration of the stock sulfurous acid solution to be added), stock $NaHSO_3$ solution, and stock $H_2SO_3$ solution. Once the cooled stock sulfurous acid solution was added to this mixture, the reactors were sealed immediately. Each reactor was cooked at the pretreatment temperature of 130° C. or 140° C., in an oil bath, for the selected pretreatment time. The pretreatment time shown includes the time for the reactor to reach the pretreatment temperature (e.g., about 5 minutes). At the end of the pretreatment, the reactors were cooled in an ice bath. All experiments conducted with or based on $SO_2$ were carried out in a fume hood.

The concentrations and conditions used are summarized in Table 1. In each case, the consistency of the slurry to be pretreated was about 10 wt %. The initial pH was measured after a 10 minute soak. The pH values were measured for runs performed in parallel (e.g., in a mock up). The first row in the table shows the concentration of $SO_2$ in the reactor, which only accounts for $SO_2$ added from stock $H_2SO_3$ solution. The second row in the table shows the concentration of $SO_2$, which accounts for $SO_2$ added from stock $H_2SO_3$ solution and from added $NaHSO_3$. The concentration of $NaHSO_3$/alkali accounts for the added $NaHSO_3$ only.

TABLE 5

Pretreatment conditions

|  | Run 1 | Run 2 | Run 3 | Run 4 |
|---|---|---|---|---|
| Concentration of $SO_2$ from $H_2SO_3$ stock (wt %, on liquor) | 7.8 | 7.8 | 10.5 | 10.5 |
| Concentration of $SO_2$ including contribution from $NaHSO_3$ (wt %, on liquor) | 8.4 | 8.4 | 11.1 | 11.1 |
| Concentration of $SO_2$ including contribution from $NaHSO_3$ (wt %, on dry weight of feedstock) | 75.5 | 75.5 | 99.7 | 99.7 |
| Concentration of $NaHSO_3$ (g/L) | 10 | 10 | 10 | 10 |
| Concentration of $NaHSO_3$ (wt %, on dry solids) | 9 | 9 | 9 | 9 |
| Concentration of alkali (wt %, OH, on liquor) | 0.16 | 0.16 | 0.16 | 0.16 |
| Ratio of concentration of SO2/alkali (where the alkali is expressed as wt % OH) | 52.5 | 52.5 | 69.4 | 69.4 |
| Pretreatment temperature (° C.) | 130 | 140 | 130 | 140 |
| Pretreatment time (min) | 60-240 | 60-180 | 60-240 | 60-180 |
| Initial pH | 0.99 | 0.99 | 0.95 | 0.95 |

A portion of the bagasse pretreated material was reserved for analysis, as described for wheat straw in Example 1. The results from the pretreatment are summarized in Table 6.

In general, the pH of the feedstock slurry drops as the pretreatment progresses. For example, for Run 1, the slurry has an initial pH of 0.99, which drops to 0.83 after 180 minutes of heating at 130° C. (e.g., a pH drop of 0.16). The magnitude of this pH drop increases as the temperature increases to 140° C. and/or when more $SO_2$ is used.

The residual xylan ($R_x$) levels are relatively low, particularly when the temperature is increased to 140° C. In general, the residual xylan is lower for lower pH values.

Remarkably, the lignin dissolution is relatively high in each case. This is remarkable for at least two reasons. First, these pretreatment conditions provide both relatively high lignin dissolution and relatively high hemicellulose dissolution (e.g., there is little evidence of a significant compromise). Second, these pretreatment conditions provide a relatively high lignin dissolution even though the initial pH of the slurry is below 1, and the final pH is as low as 0.62. Acid pretreatments, particularly at such low pH values, conventionally have been associated with lignin condensation. However, here, by using relatively high amounts of $SO_2$, in combination with $NaHSO_3$, a relatively high lignin dissolution is achieved when the pH is quite low. Remarkably, this relatively high lignin dissolution is achieved without having to use an organic solvent. Achieving a high lignin dissolution may be advantageous in terms of improving enzymatic hydrolysis and/or recovering products or byproducts.

Figure 5:
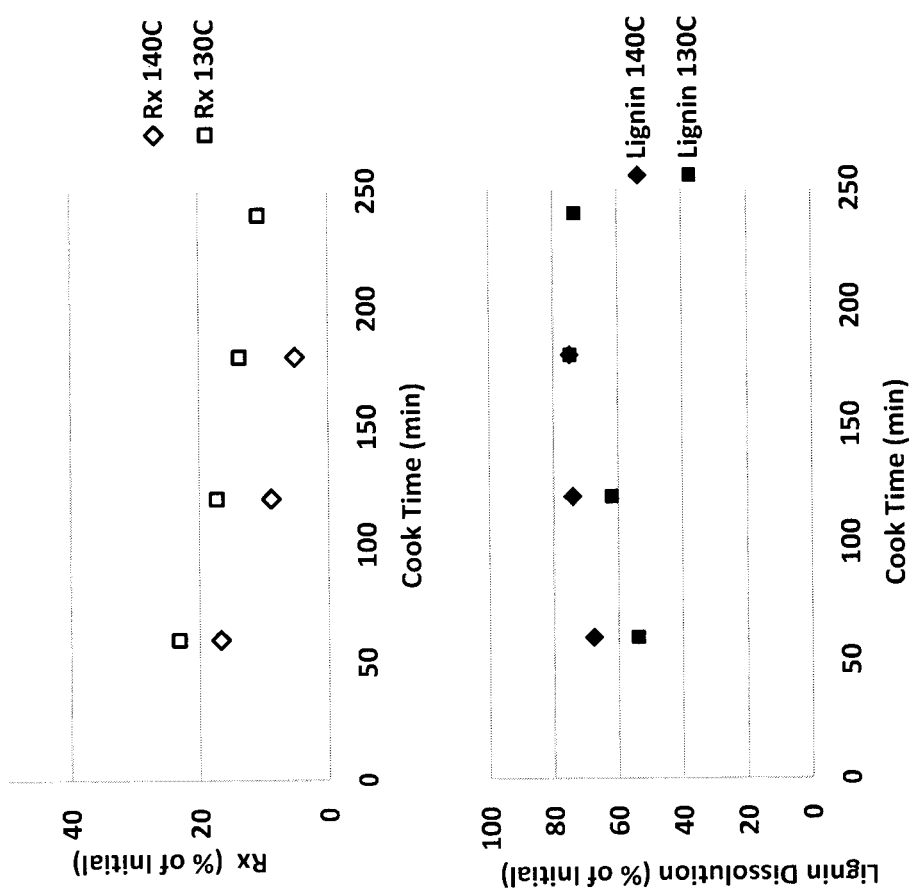
FIG. 5 shows plots of residual xylan ($R_x$) and lignin dissolution as a function of pretreatment time for the pretreatment of bagasse with $SO_2$ and $NaHSO_3$, where the concentration of $SO_2$ is 8.4 wt % on liquor and the concentration of $NaHSO_3$ is 10 g/L, at 130° C. and 140° C.
Figure 6:
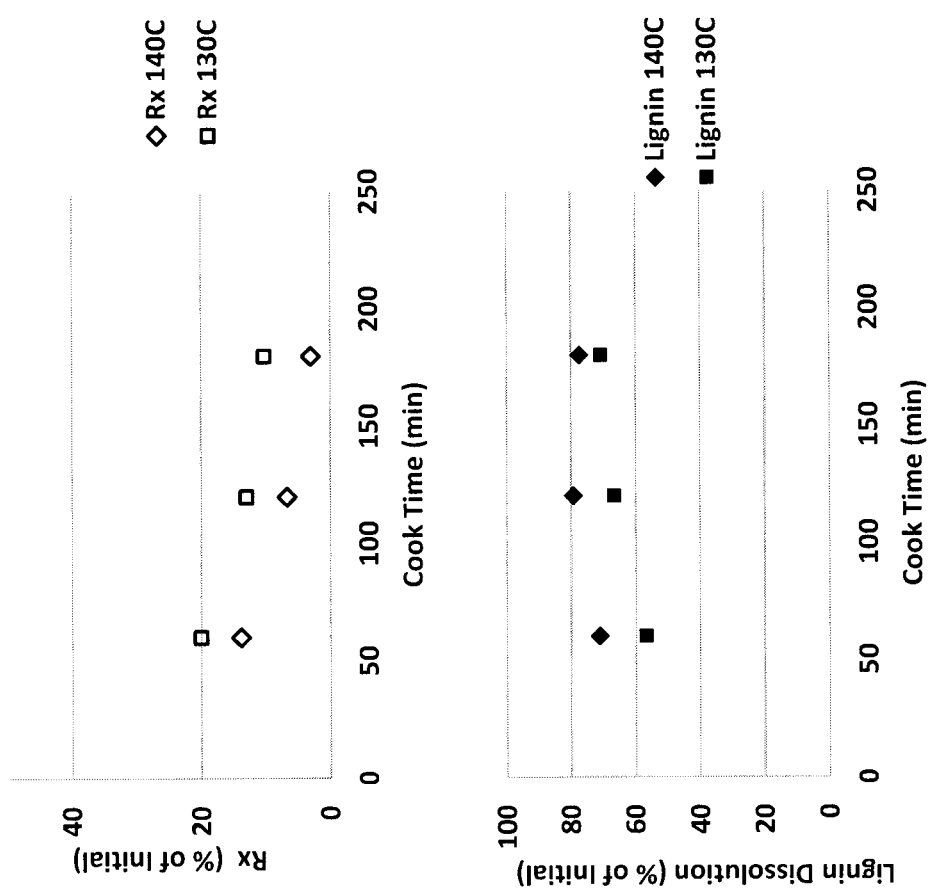
FIG. 6 shows plots of residual xylan ($R_x$) and lignin dissolution as a function of pretreatment time for the pretreatment of bagasse with $SO_2$ and $NaHSO_3$, where the concentration of $SO_2$ is 11.1 wt % on liquor and the concentration of $NaHSO_3$ is 10 g/L, at 130° C. and 140° C.

FIG. 5 shows the residual xylan ($R_x$) and lignin dissolution (as a percentage of initial) for bagasse pretreated in Runs 1 and 2 (i.e., for 8.4 wt % $SO_2$ on liquor). FIG. 6 shows the residual xylan ($R_x$) and lignin dissolution (as a percentage of initial) for bagasse pretreated in Runs 3 and 4 (i.e., for 11.1 wt % $SO_2$ on liquor). As evident from these graphs, after about 90 minutes of pretreatment these conditions provide relatively low residual xylan levels and relatively high lignin dissolution levels.

Example 4: Enzymatic Hydrolysis of Bagasse Pretreated at Low Temperature with $SO_2$ Washed pretreatment samples were prepared by suspending a portion of pretreated sample in ultra-purified water (Milli-Q™), filtering the suspension through glass fiber filter paper (G6, 1.6 microns), and then repeating the alternating steps. The washed pretreatment solids were hydrolyzed in 50 mL Erlenmeyer flasks, at a consistency of about 15 wt %, with sodium citrate (1 M of citrate buffer pH added to a final concentration of 0.1M, pH between about 5 and 5.2). The flasks were incubated at 52° C., with moderate shaking at about 250 rpm, for 30 minutes to equilibrate substrate temperature.

TABLE 6

Pretreatment results

|  | Run 1 (8.4 wt % $SO_2$, on liq at 130° C.) | Run 2 (8.4 wt % $SO_2$, on liq at 140° C.) | Run 3 (11.1 wt % $SO_2$ on liq, at 130° C.) | Run 4 (11.1 wt % $SO_2$ on liq, at 140° C.) |
|---|---|---|---|---|
| Final pH (at 180 mins) | 0.83 | 0.67 | 0.70 | 0.62 |
| Residual xylan (wt %) at 180 mins | 13.74 | 5.11 | 10.25 | 3.01 |
| Lignin solubilized (wt %) at 180 mins | 74.84 | 74.92 | 70.83 | 77.39 |
| Xylose yield (wt %) at 180 mins | 73.79 | 63.33 | (not measured) | 51.08 |

Hydrolysis was initiated by adding liquid cellulase enzyme. Enzyme was added at a dosage of 2.5 mg/g, 5 mg/g, and 9 mg/g (i.e., mg protein/g of cellulose). The flasks were incubated at 52° C. in an orbital shaker (250 rpm) for various hydrolysis times (e.g., 200 hours). The hydrolyses were followed by measuring the sugar monomers in the hydrolysate, as described in Example 2.

Figure 7:
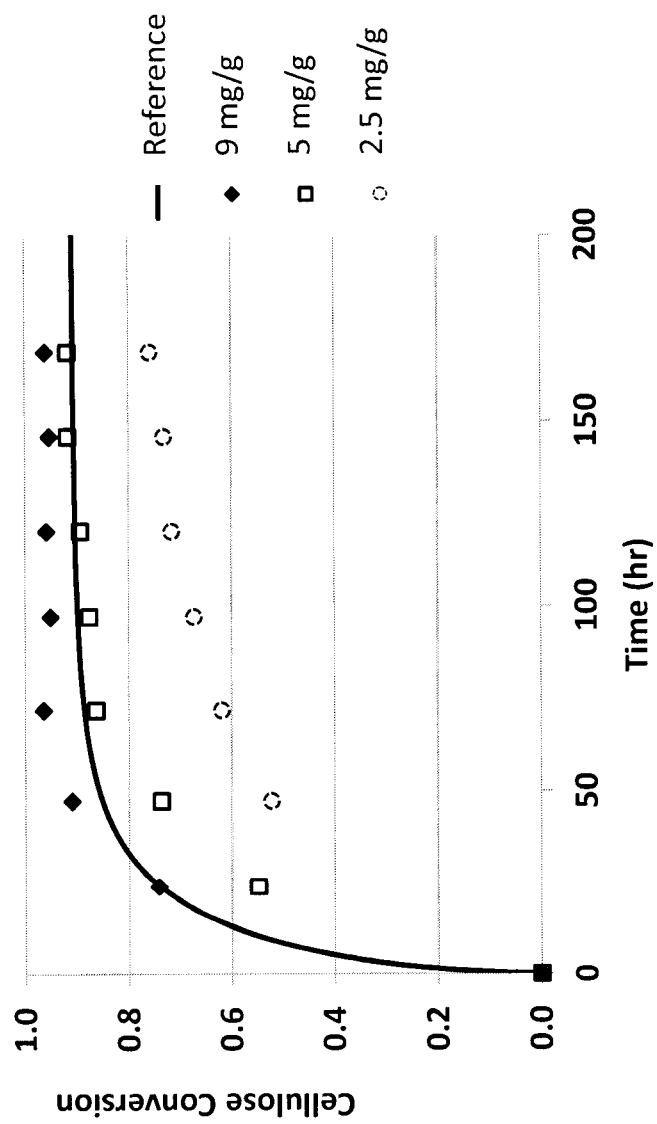
FIG. 7 is a plot of cellulose conversion versus hydrolysis time for the enzymatic hydrolysis of bagasse, where the bagasse is pretreated at 140° C. for 90 minutes, and where the concentration of $SO_2$ is 11.1 wt % on liquor and concentration of $NaHSO_3$ is 10 g/L.
Figure 8:
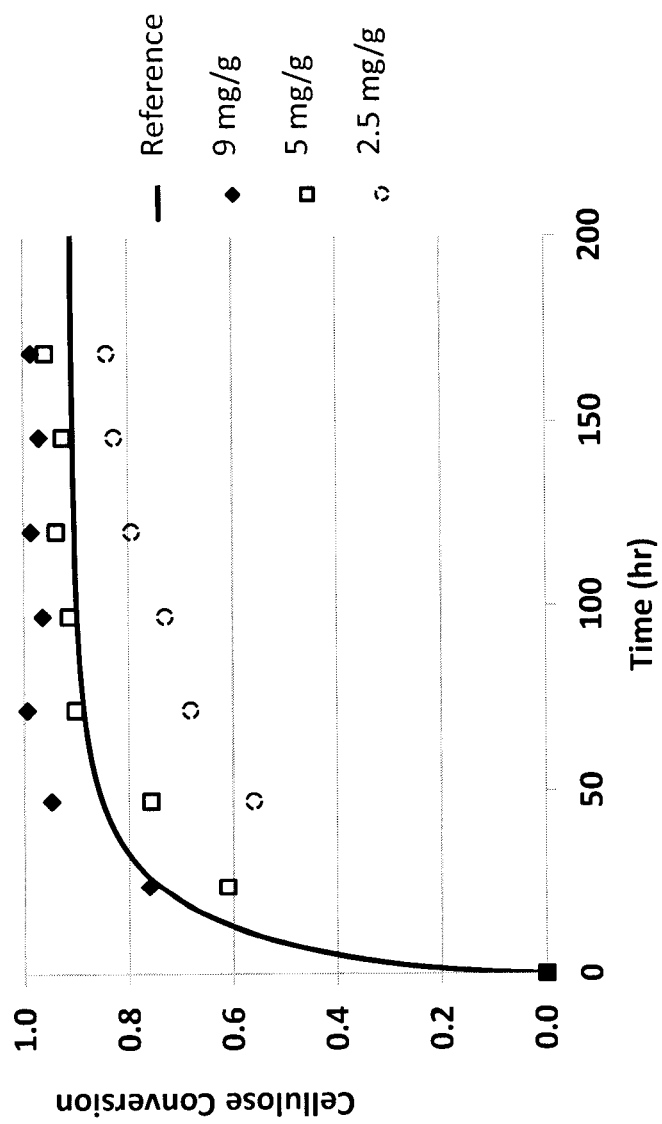
FIG. 8 is a plot of cellulose conversion versus hydrolysis time for enzymatic hydrolysis of bagasse, where the bagasse is pretreated at 140° C. for 180 minutes, where the concentration of $SO_2$ is 11.1 wt % on liquor and the concentration of $NaHSO_3$ is 10 g/L.
Figure 9:
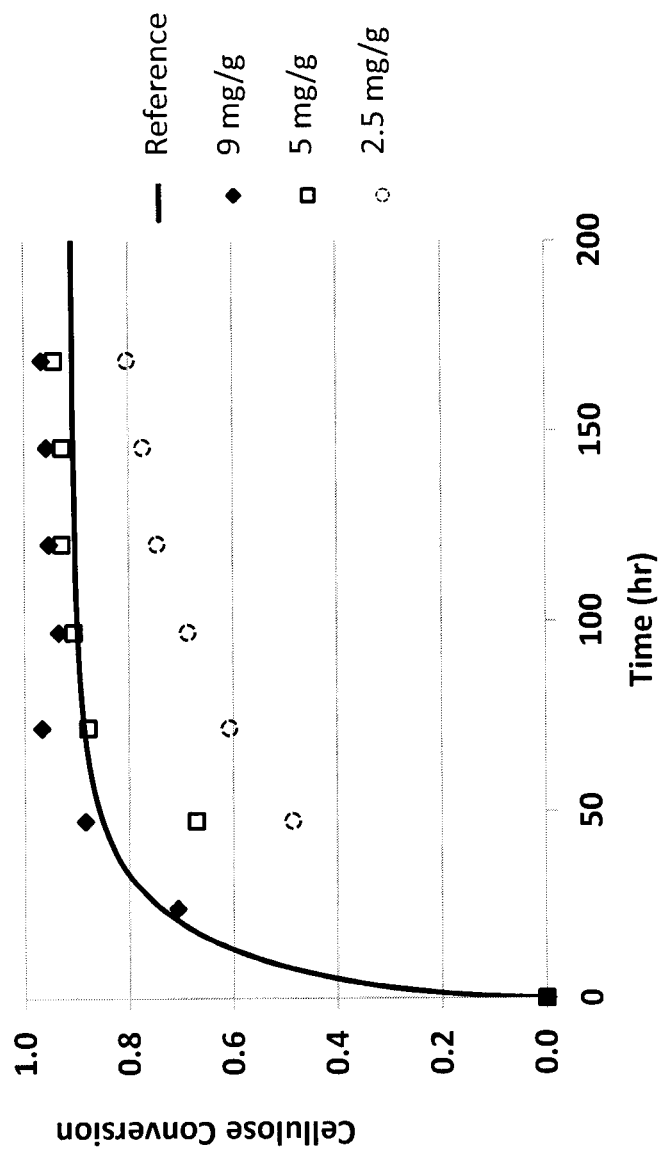
FIG. 9 is a plot of cellulose conversion versus hydrolysis time for enzymatic hydrolysis of bagasse, where the bagasse is pretreated at 140° C. for 180 minutes, where the concentration of $SO_2$ is 8.4 wt % on liquor and the concentration of $NaHSO_3$ is 10 g/L.

FIGS. 7, 8, and 9, are plots of cellulose conversion versus hydrolysis time for enzymatic hydrolysis of pretreated bagasse, where the bagasse is pretreated at 10 wt % consistency in the presence of $SO_2$ and $NaHSO_3$, where the concentration of $SO_2$ varies and the concentration of $NaHSO_3$ is 10 g/L. For references purposes, the hydrolyses were obtained using 9 mg/g, 5 mg/g, and 2.5 mg/g of enzyme, and are plotted next to the hydrolysis results of a previously optimized pretreatment of bagasse (e.g., at 10 wt % consistency, at 130° C., for 240 minutes, where the concentration of $SO_2$ was 4.7 wt % on liquor (no $NaHSO_3$)). These reference hydrolysis results, labeled reference, were obtained using 9 mg/g enzyme.

Referring to FIG. 7, the pretreatment conditions used (e.g., 8.4 wt % $SO_2$ on liquor, 140° C., 180 minutes), which corresponds to Run 2, permitted a cellulose conversion greater than 90% when 5 or 9 mg/g of enzyme was used. Notably, these hydrolysis results are superior to the previously optimized reference results. Moreover, they are obtained using a shorter pretreatment time.

Referring to FIG. 8, the pretreatment conditions used (e.g., 11.1 wt % $SO_2$ on liquor, 140° C., 180 minutes), which corresponds to Run 4, provided an increase in cellulose conversion relative to the pretreatment using lower $SO_2$ concentrations (i.e., Run 2). Advantageously, the relatively high temperature (e.g., 140° C.) and relatively high $SO_2$ concentration (e.g., 11.1 wt % on liquor), permit a cellulose conversation greater than 80% when the enzyme dose is only 2.5 mg/g. Accordingly, these pretreatment conditions can provide a high glucose yield, with smaller amounts of enzyme. This can significantly reduce the cost of the process.

Referring to FIG. 9, the pretreatment conditions used (e.g., 11.1 wt % $SO_2$ on liquor, 140° C., 90 minutes), which corresponds to shorter Run 4, permitted a high glucose yield, even when the pretreatment time is significantly reduced. In particular, by using these conditions instead of the previously optimized conditions (i.e., the reference), a higher glucose yield is obtained in less than half the pretreatment time (i.e., at the same or even lower enzyme dosage).

Without being bound by theory, the increase in temperature (e.g., to 140° C.) and/or the increase in the $SO_2$ concentration (e.g., to 11.1 wt % on liquor), may promote the formation of lignosulfonic acid. This is supported by the observed drop in pH. Lignosulfonic acid, which is a strong acid, may promote hemicellulose dissolution. This is supported by the low residual xylan ($R_x$) levels. Surprisingly, these low residual xylan levels are accompanied by a relatively high lignin dissolution (e.g., greater than about 70%). This is particularly, surprising given the low pH values of the pretreated slurry. Advantageously, this combination of relatively low residual xylan levels and high lignin dissolution can be achieved in a single stage and/or in a single pretreatment reactor. Moreover, the xylose yield does not drop too low, even when the final pH is between about 0.6 and about 0.85. Since the xylan dissolution, lignin dissolution, glucose yield, and/or xylose yield are relatively high, these pretreatment conditions provide the unique opportunity to increase the product yield from all components of the lignocellulosic biomass.

Of course, the above embodiments have been provided as examples only. It will be appreciated by those of ordinary skill in the art that various modifications, alternate configurations, and/or equivalents will be employed without departing from the spirit and scope of the invention. Accordingly, the scope of the invention is therefore intended to be limited solely by the scope of the appended claims.

The invention claimed is:

1. A process for producing a fuel from lignocellulosic biomass comprising:
   (a) obtaining a feedstock comprising lignocellulosic biomass;
   (b) feeding said feedstock and sulfur dioxide into a pretreatment reactor, wherein a total amount of sulfur dioxide in the pretreatment reactor is greater than 70 wt % based on dry weight lignocellulosic biomass;
   (c) heating the feedstock and sulfur dioxide in the pretreatment reactor at one or more temperatures between 110° C. and 150° C. for more than 60 minutes;
   (d) obtaining a slurry of pretreated material produced from (c), said slurry having a solid fraction comprising cellulose and a liquid fraction comprising solubilized hemicellulose;
   (e) hydrolyzing cellulose in the solid fraction to glucose, said hydrolyzing comprising adding cellulase to at least the solid fraction;
   (f) fermenting the glucose to a fermentation product, said fermenting comprising adding a microorganism to at least the glucose; and
   (g) recovering the fermentation product,
   wherein said fuel comprises the fermentation product,
   wherein the total amount of sulfur dioxide is sufficient to provide an initial pH between about 0.8 and 1.1, and
   wherein said heating is conducted for a time sufficient to provide a pH near the end of pretreatment that is less than 1.

2. The process according to claim 1, wherein said heating is conducted for a time sufficient to solubilize at least 50 wt % of the lignin initially present the lignocellulosic biomass.

3. The process according to claim 2, wherein said heating is conducted for a time sufficient to solubilize at least 85 wt % of the hemicellulose initially present the lignocellulosic biomass.

4. The process according to claim 1, wherein said heating is conducted above 130° C.

5. The process according to claim 1, wherein said heating is conducted between 135° C. and 145° C.

6. The process according to claim 1, wherein heating said feedstock and sulfur dioxide comprises a sulfur dioxide pretreatment wherein the amount of alkali present in the pretreatment reactor is between 0 wt % and 0.5 wt % based on dry weight of incoming lignocellulosic biomass.

7. The process according to claim 6, wherein the feedstock is selected from the group consisting of wheat straw, sugar cane bagasse, and a combination thereof.

8. The process according to claim 1, comprising feeding alkali to the pretreatment reactor, wherein the amount of alkali present in the pretreatment reactor during heating is greater than 0.05 wt % expressed as a weight percent hydroxide on liquor.

9. The process according to claim 8, wherein the feedstock is selected from the group consisting of pine, Douglas fir, and a combination thereof.

10. The process according claim 1, wherein adding enzyme comprises adding cellulase at a dosage of less than about 12 milligrams protein per gram of cellulose.

11. The process according to claim 1, wherein the fermentation product is ethanol.

12. A process for producing a fuel from lignocellulosic biomass comprising:
(a) obtaining a feedstock comprising lignocellulosic biomass;
(b) feeding said feedstock and sulfur dioxide into a pretreatment reactor, wherein a total amount of sulfur dioxide in the pretreatment reactor is sufficient to provide an initial pH that is less than 1.25 measured at ambient temperature;
(c) heating the feedstock and sulfur dioxide in the pretreatment reactor at one or more temperatures between 110° C. and 150° C. for more than 60 minutes;
(d) obtaining a slurry of pretreated material produced from (c), said slurry having a solid fraction comprising cellulose and a liquid fraction comprising solubilized hemicellulose;
(e) hydrolyzing cellulose in the solid fraction to glucose, said hydrolyzing comprising adding cellulase to at least the solid fraction;
(f) fermenting the glucose to a fermentation product, said fermenting comprising adding a microorganism to at least the glucose; and
(g) recovering the fermentation product,
wherein the fuel comprises the fermentation product
wherein said heating is conducted for a time sufficient to provide a pH near the end of pretreatment that is less than 1.

13. The process according to claim 12, wherein said heating is conducted for a time sufficient to solubilize at least 50 wt % of the lignin initially present the lignocellulosic biomass.

14. The process according to claim 13, wherein said heating is conducted for a time sufficient to solubilize at least 85 wt % of the hemicellulose initially present the lignocellulosic biomass.

15. The process according to claim 12, wherein the total amount of sulfur dioxide is sufficient to provide an initial pH between about 0.8 and 1.1.

16. The process according to claim 12, wherein said heating is conducted above 120° C.

17. The process according to claim 12, wherein said heating is conducted between 135° C. and 145° C.

18. The process according to claim 12, wherein heating said feedstock and sulfur dioxide comprises a sulfur dioxide pretreatment wherein the amount of alkali present in the pretreatment reactor is between 0 wt % and 0.5 wt % based on dry weight of incoming lignocellulosic biomass.

19. The process according to claim 12, wherein an amount of alkali present in the pretreatment reactor during heating is greater than 0.05 wt % expressed as a weight percent hydroxide on liquor.

20. The process according to claim 19, wherein the concentration sulfur dioxide in the pretreatment is greater than 7.5 wt % on liquor.

21. The process according to claim 19, wherein the concentration of sulfur dioxide in the pretreatment is between 9.4 wt % on liquor and 19.5 wt % on liquor.

22. The process according to claim 19, wherein the concentration of alkali is between about 0.1 wt % and about 0.25 wt % expressed as weight percent hydroxide on liquor.

23. The process according to claim 19, wherein a ratio of concentration of sulfur dioxide on liquor to concentration of alkali, expressed as weight percent hydroxide, on liquor is greater than 30.

24. The process according to claim 19, wherein the concentration of sulfur dioxide in the pretreatment is greater than 36 wt % on dry solids, and wherein a concentration of alkali is less than 0.25 wt % expressed as weight percent hydroxide on liquor.

25. The process according to claim 19, wherein the initial pH, at 25° C., is between 0.9 and 1.1.

* * * * *

UNITED STATES PATENT AND TRADEMARK OFFICE
CERTIFICATE OF CORRECTION

PATENT NO. : 11,345,935 B2
APPLICATION NO. : 16/761192
DATED : May 31, 2022
INVENTOR(S) : Daniel G. MacDonald It is certified that error appears in the above-identified patent and that said Letters Patent is hereby corrected as shown below:

On the Title Page

Column 1 (U.S. Patent Documents), Line 2, delete "Bois" and insert -- Du Bois --.

Page 2, Column 2 (Other Publications), Line 37, delete "S02-" and insert -- SO2- --.

Page 3, Column 2 (Other Publications), Line 43, delete "Bioresour" and insert -- Bioresource --.

Page 3, Column 2 (Other Publications), Line 54, delete "Chern." and insert -- Chem. --.

Page 3, Column 2 (Other Publications), Line 57, delete "Bioresouces," and insert -- Bioresources, --.

Page 3, Column 2 (Other Publications), Line 73, delete "Chern." and insert -- Chem. --.

Page 4, Column 1 (Other Publications), Line 1-2, delete "S02-lmpregnated" and insert -- SO2-Impregnated --.

Page 4, Column 2 (Other Publications), Line 3, delete "Celluloytic" and insert -- Cellulolytic --.

Page 4, Column 2 (Other Publications), Line 46, delete "lmpregnated" and insert -- Impregnated --.

Page 5, Column 1 (Other Publications), Line 39, delete ""S02" and insert -- "SO2 --.

In the Specification

Column 1, Line 62, delete "organsolv" and insert -- organosolv --.

Column 8, Line 55, delete "bisulfate" and insert -- bisulfite --.

Column 18, Line 23, delete "Myceliopthora," and insert -- Myceliophthora, --.

Signed and Sealed this
Eleventh Day of October, 2022

Katherine Kelly Vidal
*Director of the United States Patent and Trademark Office*

Column 18, Line 25, delete "PG," and insert -- βG, --.

Column 20, Line 53, delete "cofermenting" and insert -- co-fermenting --.

Column 28, Line 46, delete "a a" and insert -- a --.

In the Claims

Column 32, Line 43, Claim 3, after "present" insert -- in --.

Column 32, Line 65, Claim 10, after "according" insert -- to --.

Column 33, Line 32, Claim 13, after "present" insert -- in --.

Column 33, Line 36, Claim 14, after "present" insert -- in --.